US012774996B1

(12) United States Patent
Haißer et al.

(10) Patent No.: US 12,774,996 B1
(45) Date of Patent: Oct. 27, 2026

(54) METHODS OF ANALYZING LIQUID PHARMACEUTICAL COMPOSITIONS

(71) Applicant: NOVALIQ GMBH, Heidelberg (DE)

(72) Inventors: Jörg Haißer, Siegelsbach (DE); Florian Schöppler, Hockenheim (DE); Jan Bonnet, Bruchsal (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 19/417,141

(22) Filed: Dec. 11, 2025

Related U.S. Application Data

(63) Continuation of application No. 18/486,562, filed on Oct. 13, 2023.

(60) Provisional application No. 63/379,652, filed on Oct. 14, 2022.

(51) Int. Cl.
*A61K 38/13* (2006.01)
*A61K 47/06* (2006.01)
*G01N 30/12* (2006.01)
*G01N 30/74* (2006.01)
*G01N 30/89* (2006.01)
*G01N 30/02* (2006.01)

(52) U.S. Cl.
CPC ............ *G01N 30/89* (2013.01); *A61K 38/13* (2013.01); *A61K 47/06* (2013.01); *G01N 30/12* (2013.01); *G01N 30/74* (2013.01); *G01N 2030/027* (2013.01)

(58) Field of Classification Search
None
See application file for complete search history.

(56) References Cited

U.S. PATENT DOCUMENTS 6,262,126 B1 7/2001 Meinert
6,277,413 B1 * 8/2001 Sankaram .............. A61P 31/04 424/501
7,087,237 B2 8/2006 Peyman
8,614,178 B2 12/2013 Theisinger et al.
8,618,093 B2 12/2013 Chen et al.
8,669,241 B2 3/2014 Matsumura et al.
8,748,425 B2 6/2014 Chang et al.
8,796,340 B2 8/2014 Theisinger et al.
9,012,503 B2 4/2015 Tabuchi et al.
9,241,900 B2 1/2016 Wilson
9,757,459 B2 9/2017 Theisinger et al.
9,770,508 B2 9/2017 Günther et al.
9,968,678 B2 5/2018 Theisinger et al.
10,045,996 B2 8/2018 Theisinger et al.
10,058,615 B2 8/2018 Günther et al.
10,064,944 B2 9/2018 Wilson
10,286,035 B2 5/2019 Gavaris
10,369,117 B2 8/2019 Günther et al.
10,449,164 B2 10/2019 Günther et al.
10,507,132 B2 12/2019 Graf et al.
10,525,062 B2 1/2020 Theisinger et al.
10,555,953 B2 2/2020 Theisinger et al.
10,576,154 B2 3/2020 Günther et al.
10,682,315 B2 6/2020 Scherer et al.
10,813,976 B2 10/2020 Löscher et al.
11,154,513 B2 10/2021 Scherer et al.
11,160,865 B2 11/2021 Theisinger et al.
11,273,174 B2 3/2022 Löscher et al.
11,278,503 B2 3/2022 Günther et al.
11,324,757 B2 5/2022 Theisinger et al.
11,357,738 B2 6/2022 Scherer et al.
11,400,132 B2 8/2022 Löscher et al.
11,413,323 B2 8/2022 Leo et al.
11,576,893 B2 2/2023 Löscher et al.
11,583,513 B2 2/2023 Günther et al.
11,684,589 B2 6/2023 Günther et al.
11,723,861 B2 8/2023 Günther et al.
11,896,559 B2 2/2024 Günther et al.
12,005,033 B2 6/2024 Günther et al.
RE50,060 E 7/2024 Graf et al.
12,059,449 B2 8/2024 Leo et al.
12,128,010 B2 10/2024 Scherer et al.
12,150,955 B2 11/2024 Löscher et al.
12,226,422 B2 2/2025 Löscher et al.
12,496,326 B2 12/2025 Beier et al.
2006/0102561 A1 * 5/2006 Larsen ...................... A61P 3/10 210/656
2008/0193431 A1 * 8/2008 Zheng ................ A61K 41/0071 424/94.1
2016/0039760 A1 * 2/2016 Grandbois ............ B01J 31/183 546/327
2017/0087101 A1 3/2017 Scherer et al.
2018/0360908 A1 12/2018 Beier et al.

(Continued)

FOREIGN PATENT DOCUMENTS

WO 1997/012852 A1 4/1997
WO 2017/220625 A1 12/2017

OTHER PUBLICATIONS

Xu et al., "Development and Validation of a HPLC Method for Dissolution and Stability Assay of Liquid-Filled Cyclosporine Capsule Drug Products", Sep. 2013, AAPS PharmSciTech, vol. 14, No. 3, pp. 959-967. (Year: 2013).*
Xu (Year: 2013).*
"EvoTears—Gebrauchsanweisung," May 2015, retrieved from the Internet, date retrieved: Jun. 26, 2018, 2 pages, URL: http://video.apo-rot.de/docs/11213615.pdf.
"EvoTears, Product Description," 2017, Accessed Online: Dec. 27, 2023, URL: https://evotears.com/at/das-produkt/.
"Highlights of Prescribing Information VEVYE (cyclosporine ophthalmic solution) 0.1%, for topical ophthalmic use," Label—Prescribing Information, 6 pages, (2024).
"Novaliq Announces Positive Topline Results of Phase 2 Clinical Trial Evaluating CyclASol® in Adults with Moderate to Severe Dry Eye Disease," Businesswire, Jan. 5, 2017, URL: <https://www.businesswire.com/ news/home/20170105005211/en/Novaliq-Announces-Positive-Topline-Results-Phase-2>.

(Continued)

*Primary Examiner* — Paul S Hyun
(74) *Attorney, Agent, or Firm* — Hoxie & Associates LLC

(57) ABSTRACT

The present disclosure provides new methods for analyzing the active pharmaceutical ingredient or other components in a pharmaceutical composition comprising a semifluorinated alkane as the vehicle or solvent for the API.

26 Claims, 5 Drawing Sheets

(56) References Cited

U.S. PATENT DOCUMENTS

| | | | |
|---|---|---|---|
| 2019/0274970 | A1 | 9/2019 | Günther et al. |
| 2019/0321218 | A1 | 10/2019 | Graf et al. |
| 2019/0328717 | A1 | 10/2019 | Günther et al. |
| 2020/0060987 | A1 | 2/2020 | Günther et al. |
| 2020/0129543 | A1 | 4/2020 | Löscher et al. |
| 2020/0268648 | A1 | 8/2020 | Günther et al. |
| 2020/0268682 | A1 | 8/2020 | Günther et al. |
| 2021/0106558 | A1 | 4/2021 | Löscher et al. |
| 2021/0121471 | A1 | 4/2021 | Löscher et al. |
| 2021/0228595 | A1 | 7/2021 | Löscher et al. |
| 2021/0236591 | A1 | 8/2021 | Leo et al. |
| 2021/0346313 | A1 | 11/2021 | Beier et al. |
| 2022/0008397 | A1 | 1/2022 | Xu et al. |
| 2022/0031844 | A1 | 2/2022 | Mauden et al. |
| 2022/0143137 | A1 | 5/2022 | Witt et al. |
| 2022/0226426 | A1 | 7/2022 | Löscher et al. |
| 2023/0181679 | A1 | 6/2023 | Haisser et al. |

OTHER PUBLICATIONS

"Novaliq begins Phase 2 trial of Cyclasol for dry eye disease," Optometry Times, vol. 8, No. 3, (2016), p. 24.

"Novaliq GmbH Begins Phase II Clinical Trial of Cyclasol for the Treatment of Moderate to Severe Dry Eye Disease," (online), 5 pages, (2016); retrieved on Jan. 8, 2021 from the Internet: https://www.biospace.com/article/releases/novaliq-gmbh-begins-phase-il-clinical-trial-of-cyclasol-for-the-treatment-of-moderate-to-severe-dry-eye-disease-/.

"Semifluorinated alkane technology brings advantages for topical therapy," Ophthalmology Times, 2016, pp. 1-2.

"Topical drug dosage forms for eye conditions," The Pharmaceutical Journal, (Pharmaceutical Press, May 31, 2017), available at https://pharmaceutical-journal.com/article/Id/topical-drug-dosage-forms-for-eye-conditions.

Agarwal, P. et al., "Modern Approaches to the Ocular Delivery of Cyclosporine A," Drug Discovery Today, vol. 21, No. 6, pp. 977-988, (2016), doi: 10.1016/j.drudis.2016.04.002.

Agarwal, P. et al., "Semifluorinated alkane based systems for enhanced corneal penetration of poorly soluble drugs," International Journal of Pharmaceutics, vol. 538, No. 1-2, pp. 119-129, (2018).

Ahmed, S. et al., "Ocular Drug Delivery: a Comprehensive Review," AAPS PharmSciTech, vol. 24, No. 66, pp. 1-29, (2023).

Bertilla, S. et al., "Semifluorinated Alkanes as Stabilizing Agents of Fluorocarbon Emulsions," Springer, vol. 12, 24 pages, (2005).

Chaglasian, E. et al., "Recycling Cyclosporine," Review of Cornea & Contact Lenses, 2016, 5 pages.

Daull, P. et al., "Distribution of Cyclosporine A in Ocular Tissues After Topical Administration of Cyclosporine A Cationic Emulsions to Pigmented Rabbits," Cornea, vol. 32, No. 3, pp. 345-354, (2013), Abstract Only.

Dembinski, R. et al., "Semi-fluorinated Alkanes as Carriers for Drug Targeting in Acute Respiratory Failure," Experimental Lung Research, vol. 36, pp. 499-507, (2010).

Dutescu, R. et al., "Semifluorinated alkanes as a liquid drug carrier system for topical ocular drug delivery," European Journal of Pharmaceutics and Biopharmaceutics, vol. 88, No. 1, pp. 123-128, (2014).

Gehlsen, U. et al., "A semifluorinated alkane (F4H5) as novel carrier for cyclosporine A: a promising therapeutic and prophylactic option for topical treatment of dry eye," Graefe's Arch. Clin. Exp. Ophthalmol., vol. 255, No. 4, pp. 767-775, (2017).

Gehlsen. U. et al., "Cyclosporine A using F4H5 as liquid drug carrier is effective in treating experimental dry-eye disease," Investigative Ophthalmology & Visual Science, vol. 56, No. 319, 2 pages, (2015), Abstract Only.

Holm, R. et al., "A novel excipient, 1-perfluorohexyloctane shows limited utility for the oral delivery of poorly water-soluble drugs," European Journal of Pharmaceutical Sciences, vol. 42, pp. 416-442, (2011).

Kaercher, T. et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

Lallemand, F. et al., "Cyclosporine A delivery to the eye: a pharmaceutical challenge," European Journal of Pharmaceutics and Biopharmaceutics, vol. 56, No. 3, 1 page, (2003), Abstract Only.

Lallemand, F. et al., "Cyclosporine Delivery to the Eye: A comprehensive Review of Academic and Industrial Efforts," European Journal of Pharmaceutics and Biopharmaceutics, vol. 117, pp. 14-28, (2017).

Meinert, H. et al., "Semifluorinated Alkanes—A New Class of Compounds with Outstanding Properties for Use in Ophthalmology," European Journal of Ophthalmology, vol. 10, No. 3, pp. 189-197, (2000).

Meinert, H. et al., "The Use of Semifluorinated Alkanes in Blood-Substitutes," Biomaterials, Artificial Cells, and Immobilization Biotechnology, vol. 21, No. 5, pp. 583-595, (1993).

Messmer, E. et al. "Semifluorierte Alkane als Therapie bei Meibomdrüsen-Dysfunktion Ergebnisse einer prospektiven, multizentrischen Beobachtungsstudie," Presentation, DOG-Kongress, Sep. 29-Oct. 2, 2016, Berlin DOG (Deutsche Ophtalmologische Gesellschaft), Poster No. PSa03-02, 1 page (German language version).

Messmer, E. et al., "Semifluorinated Alkanes as a Therapy for Meibomian Gland Dysfunction Results of a prospective, multi-centered observational study," Presentation, DOG-Kongress, Sep. 29, 2016-Oct. 2, 2016, Berlin DOG (Deutsche Ophtalmologische Gesellschaft), Poster No. PSa03-02, English Translation, 6 pages.

Pensyl, D., "Chapter 14: Preparations for Dry Eye and Ocular Surface Disease," Clinical Ocular Pharmacology, Fifth Edition, pp. 263-278, 18 pages, (2008).

RESTASIS® Prescribing Information, available at https://www.accessdata.fda.gov/drugsatfda_docs/label/2012/050790s020lbl.pdf (Nov. 2012) (last accessed Feb. 28, 2023).

Scherer, D. et al., "Eyesol: A Novel Topical Ocular Drug Delivery System for Poorly Soluble Drugs," Drug Development & Delivery, vol. 13, No. 1, pp. 40-44, (2013).

Schmidl, D. et al., "Influence of Perfluorohexyloctane Eye Drops on Tear Film Thickness in Patients with Mild to Moderate Dry Eye Disease: A Randomized Controlled Clinical Trial," Journal of Ocular Pharmacology and Therapeutics, vol. 36, No. 3, 8 pages, (2020).

Sheppard, J. et al., "A Water-free 0.1% Cyclosporine A Solution for Treatment of Dry Eye Disease: Results of the Randomized Phase 2B/3 Essence Study," Cornea, vol. 40, No. 10, pp. 1290-1297, (2021).

Steven, P. et al., "Semifluorinated Alkane Eye Drops for Treatment of Dry Eye Disease—A Prospective, Multicenter Noninterventional Study" Investigative Ophthalmology & Visual Science, vol. 56, No. 4493, 1 page, (2015), Abstract Only.

Steven, P. et al., "Semifluorinated Alkane Eye Drops for Treatment of Dry Eye Disease—A Prospective, Multicenter Noninterventional Study," Journal of Ocular Pharmacology and Therapeutics, vol. 31, No. 8, pp. 498-503, (2015).

Steven, P. et al., "Semifluorinated Alkane Eye Drops for Treatment of Dry Eye Disease Due to Meibomian Gland Disease," Journal of Ocular Pharmacology and Therapeutics, vol. 33, No. 9, pp. 1-8, (2017).

Tauber, J. et al., "A Randomized Clinical Study (SEECASE) to Assess Efficacy, Safety, and Tolerability of NOV03 for Treatment of Dry Eye Disease," Cornea, vol. 40, No. 9 , pp. 1132-1140, (2021).

Wong, D. et al., "Perfluorocarbons and Semifluorinated Alkanes," Seminars in Ophthalmology, vol. 15, No. 1, pp. 25-35, (2000).

* cited by examiner

METHODS OF ANALYZING LIQUID PHARMACEUTICAL COMPOSITIONS

CROSS-REFERENCE TO RELATED APPLICATIONS

This Application is a continuation of U.S. non-provisional patent application Ser. No. 18/486,562, filed on Oct. 13, 2023, which claims priority to, and the benefit of, U.S. Provisional Application Ser. No. 63/379,652, filed on Oct. 14, 2022, the contents of each of which are hereby incorporated by reference in their entireties.

BACKGROUND OF THE INVENTION

Keratoconjunctivitis sicca, also known as dry eye disease or dysfunctional tear syndrome, is today understood as a multifunctional disorder of the tear film and of the ocular surface which results in discomfort, visual disturbance, and often even in ocular surface damage caused by tear film instability. Estimates of the prevalence of dry eye vary considerably, depending on the criteria used to define the disease, but in the U.S., it has been estimated that as many as 3.2 million women and 1.7 million men over the age of 50 have dry eye, with a projected 40% increase in number of patients affected by 2030.

An established pharmacological treatment option for dry eye disease is cyclosporine (also known as ciclosporin, cyclosporin A, or CsA). Cyclosporine is available in the U.S. as an approved medicine in the form of an aqueous ophthalmic (oil in water, o/w) emulsion (Restasis®). This product is indicated to increase tear production in patients whose tear production is presumed to be suppressed due to ocular inflammation associated with keratoconjunctivitis sicca.

Cyclosporin is a challenging compound to formulate and to deliver due to its extremely poor solubility in water, and relatively large molecular size (molecular weight 1202.61 Da). Solubilizing excipients such as surfactants and organic or oil-based solvents are typically required in formulations of this compound.

U.S. Pat. No. 8,614,178 discloses pharmaceutical compositions in the form of solutions comprising cyclosporine and a semifluorinated alkane (SFA) as a liquid vehicle which may be administered to the eye of a patient, such as for the treatment of keratoconjunctivitis sicca, for instance compositions comprising cyclosporine in the semifluorinated alkane 1-perfluorobutyl-pentane (F4H5) in the presence of ethanol as a co-solvent. U.S. Pat. No. 8,614,178, however, does not describe dosing and treatment regimen for the treatment of dry eye disease, in particular moderate to severe dry eye disease and associated conditions.

Gehlsen et al. (Investigative Ophthalmology & Visual Science June 2015, Vol. 56, 319) describes a study to test the use of CsA in SFA (F4H5) as a carrier for topical therapy in a mouse model of experimental dry eye disease. Gehlsen et al. describes that in the study, topical therapy was performed on mice with induced experimental dry eye disease 3×/day (5 μL/eye).

It is disclosed that cyclosporin has a solubility of 2.54 g/L in the semifluorinated alkane 1-perfluorobutyl-pentane (F4H5), in the absence of any co-solvent. U.S. Pat. No. 8,614,178 further teaches that with a small amount of ethanol as a co-solvent, the solubility of ciclosporin in F4H5 increases markedly, for example, to 5.65 g/L when 1.0 wt. % of ethanol is included in the composition. Ethanol is, generally speaking, not well tolerated by the human eye, however, it is mentioned that inclusion of a small amount of ethanol, such as 1 wt. %, does not adversely affect tolerability. It is preferable, nevertheless, if cyclosporine can be formulated in the absence of excipients or co-solvents.

U.S. Pat. No. 10,813,976 discloses ophthalmic pharmaceutical compositions in the form of a clear solution comprising cyclosporin dissolved in 1-perfluorobutyl-pentane (F4H5), wherein the water content of the cyclosporine used in the composition is less than 1 wt. %. U.S. Pat. No. 10,813,976 further teaches an ophthalmic pharmaceutical composition in the form of a clear solution comprising cyclosporin dissolved in 1-perfluorobutyl-pentane (F4H5), wherein the composition is essentially free of a co-solvent or excipient.

U.S. 2018/0360908 discloses the treatment of dry eye disease utilizing ophthalmic compositions comprising 0.05-0.1% (w/v) cyclosporine dissolved in a vehicle comprising 1-perfluorobutyl-pentane (F4H5) and up to 1 wt. % ethanol.

Such cyclosporine ophthalmic pharmaceutical compositions may be developed as a medical treatment, in particular for use in the treatment of keratoconjunctivitis sicca, meibomian gland dysfunction, or a symptom thereof. In particular, these compositions may find use for topical administration to the eye, such as in the form of eye drops.

One challenge of seeking regulatory approval for such a composition is developing a reliable method of assaying such a composition to determine its purity. Nearly all currently approved liquid pharmaceutical compositions, including both eye drops and injectables, are either aqueous solutions or aqueous emulsions (e.g., oil-in-water emulsions). There are no currently marketed pharmaceutical products having an active pharmaceutical ingredient (API) dissolved or otherwise dispersed in any fluorinated or semifluorinated hydrocarbon solvent. Consequently, there are no described methods for determining the content of either API or other components (excipients or impurities) in such a vehicle (i.e., assaying). Indeed, it is a prerequisite for regulatory approval in any country that an assay method exists that can be applied to ensure that such compositions are correctly formulated for safe and efficacious administration to patients.

High-pressure liquid chromatography (HPLC) analysis, such as reverse-phase HPLC, is the current method of choice for the determination of the assay and purity of active pharmaceutical ingredients in commercial pharmaceutical compositions. In any HPLC procedure, an analyte solution is introduced onto a fixed column containing a bound, stationary phase material. A mobile phase solvent runs through the column, and due to interactions between the analyte and the stationary phase, the individual components of the analyte become separated as they progress through the column, ultimately eluting from the bottom of the column at different time points. The rate at which a particular component of the analyte moves through the column depends on its relative attraction to the stationary phase versus the mobile phase. A constituent that is more soluble in the mobile phase will move through the column faster, while a component which is more strongly attracted to the stationary phase will move through the column slower. Thus, the time point at which a particular component elutes from the column can be correlated to the identity of the component by reference to standard samples. Each component of the analyte can be detected as it elutes off the column, often by means of spectroscopy (e.g., ultraviolet/visible light spectroscopy, PDA (photo diode array), fluorescence) or by means of other detectors (e.g., refractive index, evaporative light scattering, multi-angle light scattering, conductivity, chemiluminescence, optical rotation, or other electro-chemical methods).

HPLC generally falls into two categories: normal phase and reverse phase. In normal phase HPLC, the stationary phase is highly hydrophilic (e.g., silica gel or alumina) and the mobile phase is a hydrophobic organic solvent (e.g., hexane, ethyl acetate). In reverse phase HPLC, the polarity of the phases is reversed—the stationary phase is hydrophobic (e.g., polymeric resins having hydrocarbon surface groups) and the mobile phase is hydrophilic (e.g., methanol, water, acetonitrile). For loading onto such columns, analytes are typically diluted with a solvent compatible (i.e., miscible with, and preferably similar in polarity to) the mobile phase.

Most of the analytical methods for assay and purity determination of API described in the pharmacopoeias are reverse-phase HPLC methods, because most API are highly soluble in reverse-phase HPLC compatible solvents (e.g., water and alcohols). In addition, as nearly all regulatory approved liquid pharmaceutical compositions are aqueous-based, reverse-phase HPLC is the best choice for separating the composition's components. There is thus an extensive collective experience of pharmaceutical chemists and other scientists in predicting the behavior of typical API organic molecules dissolved in aqueous mixtures during reverse-phase HPLC.

Analysis of the pharmaceutical composition of the present disclosure is made difficult because these compositions are anhydrous compositions comprising a semifluorinated alkane vehicle. There has been little to no reporting of the behavior of semifluorinated alkane solvents in HPLC systems, and it was therefore not known how API would behave dissolved in semifluorinated alkane as it passes through an HPLC column, or how the semifluorinated alkane itself would interact with the stationary phase and the mobile phase of the column. As there has not been any medicinal product commercialized prior to the earliest filing date of the instant application which comprises any active pharmaceutical ingredient dissolved in a semifluorinated alkane, the prior art appears to be silent as to how to reliably assay such compositions.

The present inventors have found that traditional methods for assaying aqueous solutions—including reverse-phase HPLC using a stationary hydrophobic phase and an aqueous mobile phase—do not work for active pharmaceutical ingredients dissolved in a semifluorinated alkane. It was unexpectedly found that introducing an SFA-based analyte onto a reverse-phase HPLC column results in interference and disruption of the expected column dynamics leading to unreliable results.

As such, a need has existed for new methods which enable the assaying of a liquid, pharmaceutical solution comprising an active pharmaceutical ingredient dissolved in a semifluorinated alkane solvent. In particular, a need has existed for reliable methods for assaying cyclosporin dissolved in semifluorinated alkane vehicles. The aim of the present disclosure is to satisfy this need.

BRIEF SUMMARY

In a first aspect, the present disclosure provides a method of determining the content of an active pharmaceutical ingredient (API) in a liquid pharmaceutical composition comprising the API dissolved or otherwise dispersed in a semifluorinated alkane (SFA) vehicle.

In a second aspect, the present disclosure provides a method of determining the contents of a liquid pharmaceutical composition comprising an SFA vehicle, e.g., the API, the SFA, any excipients or solvents, and/or any impurities. In some embodiments of the second aspect, the method makes a determination of the purity of the liquid pharmaceutical composition (e.g., percent purity).

In a third aspect, the present disclosure provides a method of manufacturing a liquid pharmaceutical composition comprising an API dissolved, suspended, or dispersed in an SFA, which comprises the step of analyzing a lot sample of the composition for the content of the API or any other components contained in the composition.

In some embodiments of the foregoing aspects, the SFA is selected from a solvent having the general formula RFRH, wherein RF represents a perfluoroalkyl segment having 2 to 10 carbon atoms, and RH represents a non-fluorinated alkyl segment having 2 to 12 carbon atoms, for example, an SFA selected from the group consisting of F4H5, F4H8, F6H2, F6H6 and F6H8. In some embodiments of the foregoing aspects, the API is cyclosporin A.

The present inventors' work has contributed to the regulatory approval of VEVYE®, the first ever approved medicinal composition comprising an active pharmaceutical ingredient in a semifluorinated alkane vehicle. VEVYE® is a water-free, liquid ophthalmic solution for administration to the surface of the eye comprising 0.1% (w/v) cyclosporine A dissolved in F4H5 with 1.0% (w/w) ethanol. VEVYE® was approved in May 2023 by the U.S. FDA for the treatment of the signs and symptoms of dry eye disease.

DETAILED DESCRIPTION

Figure 1:
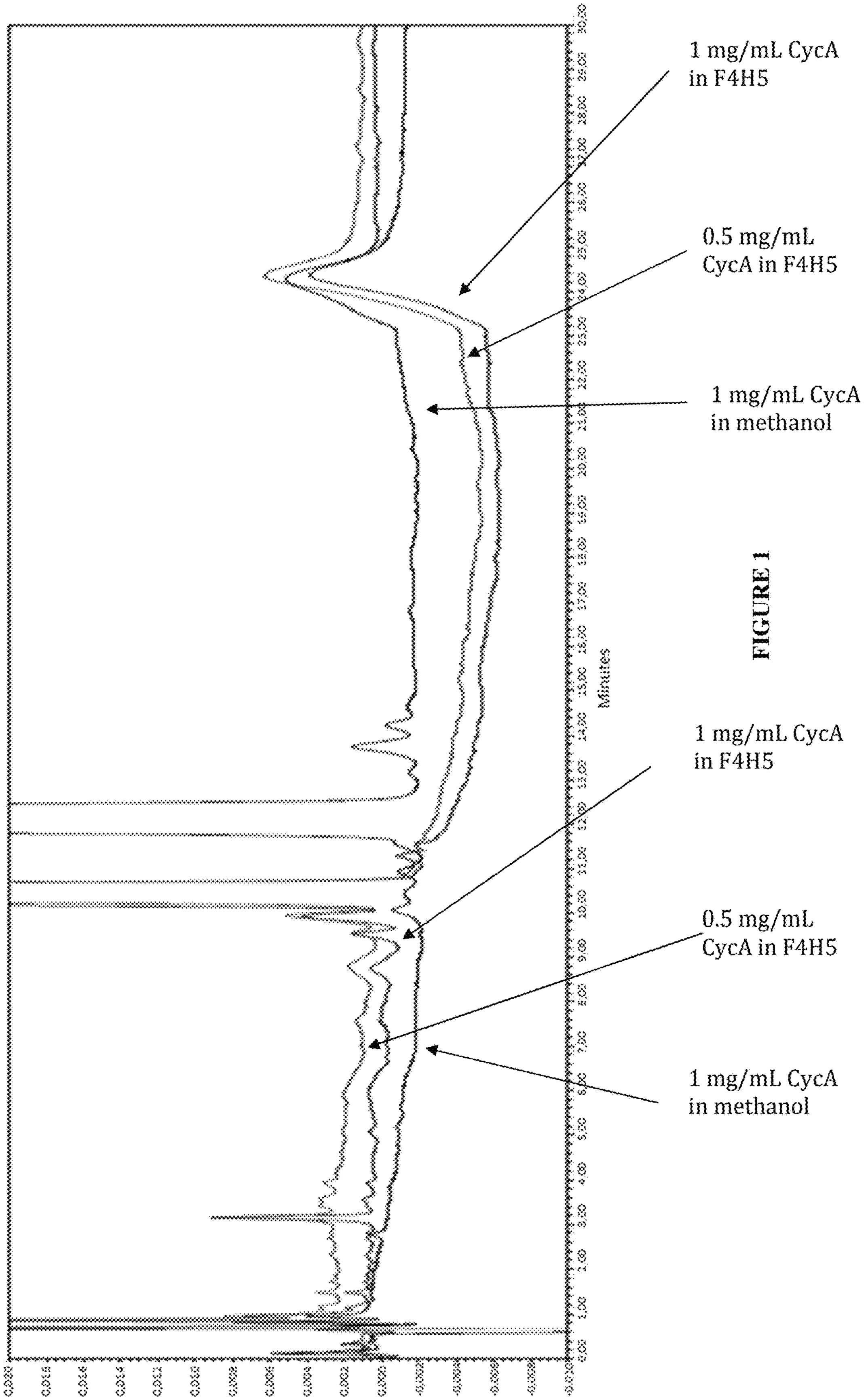
FIG. 1. HPLC chromatograms resulting from direct injection of 0.5 mg/mL and 1.0 mg/mL cyclosporin A (CycA) solutions in F4H5 solvent, in comparison to reference 1 mg/mL cyclosporin A in methanol (see Example 1).

In a first aspect, the present disclosure provides a method (Method 1) of determining the content of an active pharmaceutical ingredient (API) in a liquid pharmaceutical composition comprising the API dissolved or otherwise dispersed in a semifluorinated alkane (SFA) vehicle. In further embodiments of the first aspect, the present disclosure provides:

1.1 Method 1, wherein the pharmaceutical composition comprises the API dissolved, dispersed or suspended in a liquid vehicle comprising the SFA (e.g., at least one SFA).

1.2 Method 1.1, wherein the liquid vehicle comprises at least 50% v/v of the SFA, e.g., at least 60% v/v, or at least 70% v/v, or at least 80% v/v, or at least 85% v/v, or at least 90% v/v, or at least 95% v/v, or at least 96% v/v, or at least 97% v/v, or at least 98% v/v, or at least 99% v/v, of the SFA.

1.3 Method 1.1 or 1.2, wherein the liquid vehicle further comprises a non-SFA co-solvent (e.g., ethanol).

1.4 Method 1.3, wherein the liquid vehicle comprises the non-SFA co-solvent (e.g., ethanol) in an amount of not more than 5% v/v, e.g., 0.1-2% v/v or 0.5-1.5% or about 1% v/v.

1.5 Method 1, or any of 1.1-1.4, wherein the liquid vehicle comprises a second SFA that is different than the first SFA, optionally with a non-SFA co-solvent.

1.6 Method 1.5, wherein the second SFA is a structural isomer of the first SFA.

1.7 Method 1.5 or 1.6, wherein the vehicle consists of a first SFA, optionally a second SFA, and optionally a non-SFA co-solvent.

1.8 Method 1.7, wherein the vehicle consists of a first SFA, a second SFA which is a structural isomer of the first SFA, and ethanol.

1.9 Method 1.7 or 1.8, wherein the vehicle consists of at least 97% v/v of the first SFA and not more than 1% v/v of the second SFA and not more than 2% v/v of the non-SFA cosolvent (e.g., ethanol), e.g., at least 98% v/v of the first SFA and not more than 0.5% v/v of the second SFA and not more than 1% v/v of the non-SFA cosolvent (e.g., ethanol).

1.10 Method 1.7, wherein the vehicle consists of at least 99% v/v of the first SFA and not more than 0.5% v/v of the second SFA and no non-SFA cosolvent (e.g., no ethanol).

1.11 Method 1, or any of 1.1 et seq., wherein method comprises an analytical step of reverse-phase high-pressure liquid chromatography (RP-HPLC).

1.12 Method 1, or any of 1.1 et seq., wherein the method comprises the step of removing a portion of (e.g., all or substantially all) of the liquid vehicle of the composition before submission to RP-HPLC analysis (e.g., before injection onto the RP-HPLC column).

1.13 Method 1.12, wherein at least 50% of the volume of the liquid vehicle is removed, e.g., at least 60%, or at least 70%, or at least 80%, or at least 90%, or at least 95%, or at least 97% or at least 99%.

1.14 Method 1.12 or 1.13, wherein the removal step comprises evaporation of the liquid vehicle, optionally under vacuum and/or under elevated temperature (e.g., >30° C.).

1.15 Method 1, or any of 1.1 et seq., wherein the method comprises the steps of:

a. Taking a representative sample of the pharmaceutical composition;

b. Removing a portion of the liquid vehicle from the pharmaceutical composition, e.g., by evaporation to yield a residue;

c. Dissolving the residue in a suitable injection solvent to form the injection sample;

d. Causing the injection sample to be introduced onto a reverse-phase high-pressure liquid chromatography (HPLC) column comprising a stationary phase;

e. Causing a liquid mobile phase to un through the column in order to separate and elute the components of the pharmaceutical composition;

f. Detecting the components eluting off the column, e.g., using at least ultraviolet detection;

g. Determining the amount of the API in the pharmaceutical composition sample (e.g., as a percent of the theoretical amount or an absolute amount).

1.16 Method 1, or any of 1.1 et seq., comprising the step of quantifying the content of the active pharmaceutical ingredient (API) comprised in the pharmaceutical composition.

1.17 Method 1.16, wherein the quantification of the content of the active pharmaceutical ingredient (API) is based on the peak corresponding to the active pharmaceutical ingredient (API).

1.18 Method 1.17, wherein the quantification of the content of the active pharmaceutical ingredient (API) is based on integration of the peak area (area under the peak) of the peak corresponding to the active pharmaceutical ingredient (API).

1.19 Method 1, or any of 1.1 et seq., wherein the pharmaceutical composition comprises at least 25% by weight of the SFA, e.g., at least 50% by weight, or at least 75% by weight, or at least 80% by weight, or at least 85% by weight, or at least 90% by weight, or at least 95% by weight, of the SFA.

1.20 Method 1, or any of 1.1 et seq., wherein the pharmaceutical composition comprises at least 95% by weight of the SFA, e.g., at least 97% or at least 98% or at least 99%, by weight, of the SFA.

1.21 Method 1, or any of 1.1 et seq., wherein the API is selected from cyclosporin, tacrolimus, sirolimus, and everolimus, e.g., the API is cyclosporin A.

1.22 Method 1, or any of 1.1 et seq., wherein the pharmaceutical composition consists essentially of cyclosporin A and the SFA.

1.23 Method 1.22, wherein the pharmaceutical composition consists of cyclosporin A and the SFA.

1.24 Method 1, or any of 1.1 et seq., wherein the SFA has the general formula RFRH, wherein RF represents a perfluoroalkyl segment having 2 to 10 carbon atoms, and RH represents a non-fluorinated alkyl segment having 2 to 12 carbon atoms.

1.25 Method 1, or any of 1.1 et seq., wherein the SFA is selected from the group consisting of F2H4, F4H5, F6H2, F6H6, and F6H8.

1.26 Method 1, or any of 1.1 et seq., wherein the SFA is F4H5 (1-perfluorobutylpentane).

1.27 Method 1, or any of 1.1 et seq., wherein the composition (e.g., the vehicle) comprises a single SFA (e.g., F4H5).

1.28 Method 1, or any of 1.1 et seq., wherein the composition (e.g., the vehicle) comprises a first SFA and second SFA (i.e., which are different SFAs) (e.g., wherein at least one is F4H5).

1.29 Method 1.28, wherein the second SFA is a structural isomer of the first SFA (e.g., one SFA is linear and the other SFA is branched, but both SFAs have the same chemical formula).

1.30 Method 1.29, wherein the first SFA is 1-perfluorobutylpentane and the second SFA is 2-perfluorobutylpentane.

1.31 Method 1.29, 1.30 or 1.31, wherein the composition comprises at least 75% by weight of the first SFA and not more than 25% by weight of the second SFA, for example, at least 80% by weight of the first SFA and not more than 20% by weight of the second SFA, or at least 85% by weight of the first SFA and not more than 15% by weight of the second SFA, or at least 90% by weight of the first SFA and not more than 10% by weight of the second SFA, or at least 95% by weight of the first SFA and not more than 5% by weight of the second SFA, or at least 97% by weight of the first SFA and not more than 3% by weight of the second SFA, or at least 98% by weight of the first SFA and not more than 2% by weight of the second SFA (e.g. 0.2%, or 0.4%, or 0.6%, or 0.8%, or 1.0%, or 1.2%, or 1.4%, or 1.6%, or 1.8%, or 2.0% of the second SFA), or at least 97% by weight of the first SFA and not more than 1% by weight of the second SFA (e.g. 0.2%, or 0.4%, or 0.6%, or 0.8%, or 1.0% of the second SFA, or at least 97% by weight of the first SFA and not more than 0.5% by weight of the second SFA (e.g. 0.2%, or 0.3%, or 0.4%, or 0.5% of the second SFA), or at least 97% by weight of the first SFA and not more than 0.4% by weight of the second SFA (e.g., 0.2%, or 0.3% or 0.4% of the second SFA).

1.32 Method 1, or any of 1.1 et seq., wherein the composition does not comprise any excipients or co-solvents.

1.33 Method 1, or any of 1.1 et seq., wherein the composition comprises up to 1.0 wt. % of ethanol as co-solvent.

1.34 Method 1, or any of 1.1 et seq., wherein the pharmaceutical composition consists essentially of cyclosporin A, the SFA (e.g., F4H5) and ethanol.

1.35 Method 1 or any of 1.1 et seq., wherein the pharmaceutical composition consists of cyclosporin A the SFA (e.g., F4H5) and ethanol.

1.36 Method 1, or any of 1.1 et seq., wherein the composition comprises from 0.01 to 1.1% w/v of the API (e.g., cyclosporin), e.g., about 1.0% w/v.

1.37 Method 1, or any of 1.1 et seq., wherein the composition comprises from 0.01 to 0.55% w/v of the API (e.g., cyclosporin), e.g., about 0.5% w/v.

1.38 Method 1, or any of 1.1 et seq., wherein the composition comprises from 0.01 to 0.15% w/v of the API (e.g., cyclosporin), e.g., about 0.10% w/v.

1.39 Method 1, or any of 1.1 et seq., wherein the composition comprises from 0.01 to 0.06% w/v of the API (e.g., cyclosporin), e.g., about 0.05% w/v.

1.40 Method 1, or any of 1.1 et seq., wherein the composition comprises or essentially consists of 0.05-0.10% (w/v) cyclosporin A, dissolved in 1-perfluorobutylpentane and up to about 1 wt. % ethanol.

1.41 Method 1, or any of 1.1 et seq., wherein the composition comprises or essentially consists of 0.05% (w/v) cyclosporin A, dissolved in 1-perfluorobutylpentane and up to about 1 wt. % ethanol.

1.42 Method 1, or any of 1.1 et seq., wherein the composition comprises or essentially consists of 0.10% (w/v) cyclosporin A, dissolved in 1-perfluorobutylpentane and up to about 1 wt. % ethanol.

1.43 Method 1, or any of 1.1 et seq., wherein the composition comprises or essentially consists of 0.10% (w/v) cyclosporine A, not less than 97% wt. % F4H5, not more than 0.5 wt. % 2-perfluorobutylpentane, and up to about 1 wt. % ethanol, wherein the cyclosporine A is dissolved to form a solution (e.g., a clear solution). Method 1, or any of 1.1 et seq., wherein the composition comprises or essentially consists of 0.10% (w/v) cyclosporine A, not less than 97% wt. % F4H5, not more than 0.5 wt. % 2-perfluorobutylpentane, with no co-solvent (e.g., no ethanol), wherein the cyclosporine A is dissolved to form a solution (e.g., a clear solution).

1.44 Method 1, or any of 1.1 et seq., wherein the composition comprises or essentially consists of 0.05% (w/v) cyclosporine A, not less than 97% wt. % F4H5, not more than 0.5 wt. % 2-perfluorobutylpentane, and up to about 1 wt. % ethanol, wherein the cyclosporine A is dissolved to form a solution (e.g., a clear solution).

1.45 Method 1, or any of 1.1 et seq., wherein the composition comprises or essentially consists of 0.05% (w/v) cyclosporine A, not less than 97% wt. % F4H5, not more than 0.5 wt. % 2-perfluorobutylpentane, with no co-solvent (e.g., no ethanol), wherein the cyclosporine A is dissolved to form a solution (e.g., a clear solution).

1.46 Method 1, or any of 1.1 et seq., wherein the composition is formulated for and/or approved for use as a topical ophthalmic eye drop.

1.47 Method 1.46, wherein the composition is formulated for and/or approved for application to the surface of the cornea and/or the conjunctiva.

1.48 Method 1.46 or 1.47, wherein the composition is formulated for and/or approved for use at a dosage of a single drop in each eye one to four times per day, e.g., once, twice or three times per day, e.g., for use at a dosage of a single drop in each eye two times per day.

1.49 Method 1.48, wherein the drop volume is 8 to 11 μL, or 8 to 10 μL, or 9 to 10 μL or about 10 μL.

1.50 Method 1.46, 1.47, 1.48 or 1.49, wherein the composition is formulated for and/or approved for the treatment of keratoconjunctivitis sicca (dry eye disease), or the signs and symptoms of keratoconjunctivitis sicca (dry eye disease), meibomian gland dysfunction (MGD), blepharitis, ocular surface damage, uveitis, ocular allergy, ocular neovascularization, intraocular inflammatory disease, or any symptoms associated with the foregoing.

1.51 Method 1, or any of 1.1 et seq., wherein the injection solvent of step (c) is water-acetonitrile mixture, e.g., about a 50:50 v/v mixture.

1.52 Method 1, or any of 1.1 et seq., wherein the mobile phase of step (e) comprises an elution gradient of a water-acetonitrile mixture, e.g., a gradient running from about 65% water/35% acetonitrile to about 35% water/65% acetonitrile (or a gradient running from about 65% water/35% acetonitrile to about 40% water/60% acetonitrile), followed by a column purge to return to initial conditions (e.g., a ten-minute purge with 65% water/35% acetonitrile, or a ten minutes purge with 10% water/90% acetonitrile followed by a ten-minute purge with 65% water/35% acetonitrile), optionally wherein the mobile phase further comprises about 0.05-0.10% v/v of an acid, e.g., phosphoric acid.

1.53 Method 1, or any of 1.1 et seq., wherein the stationary phase of the column of step (d) is a modified silica, e.g., high-purity porous silica having chemically bonded surface groups (e.g., isopropyl and/or nitrile groups).

1.54 Method 1.53, wherein the stationary phase of the column of step (d) is high-purity porous silica having chemically bonded nitrile groups, e.g., a stationary phase conforming to U.S. Pharmacopeia Method L10 (such as the Agilent SB-CN column series).

1.55 Method 1, or any of 1.1 et seq., wherein detection of step (f) is performed using a wavelength of 180 to 230 nm (e.g., 210 nm wavelength).

1.56 Method 1, or any of 1.1 et seq., wherein step (b) is performed by subjecting the sample to a stream of a gas, such as an inert gas, e.g., nitrogen or argon, to evaporate the vehicle (e.g., the SFA, e.g., F4H5).

1.57 Method 1, or any of 1.1 et seq., wherein step (b) is performed by vacuum evaporation, e.g., by subjecting the sample to a reduced pressure (e.g., a pressure below the vapor pressure of the vehicle), such to evaporate or support the evaporation of the vehicle (e.g., the SFA, e.g., F4H5 and/or ethanol).

1.58 Method 1.57, wherein the evaporation takes place at 25-50° C. (e.g., about 30° C.), for 30 to 500 minutes (e.g., at least 60 minutes).

1.59 Method 1, or any of 1.1 et seq., wherein:

a. The stationary phase of the column has particles having an average particle size diameter of 1-10 microns, or 1.5-10 microns, or 1.8-10 microns, or 3 to 10 microns, e.g., 1.8, or 3.5 or 5 microns; and/or b. The stationary phase of the column has particles having an average pore size of 50 to 500 Angstroms, e.g., 250 to 500 Angstroms, or 150 to 450 Angstroms, or 250 to 350 Angstroms, about 300 Angstroms, or about 80 Angstroms; and/or c. The mobile phases comprise about 0.08% v/v of 85% phosphoric acid; and/or d. The injection sample volume is about 20 microliters; and/or e. The mobile phase flow rate is about 1 mL/minute; and/or f. The column has a length of packed stationary phase of 15 to 250 mm, e.g., 250 mm; and/or g. The representative sample of the pharmaceutical composition is about 600 microliters, and the residue is redissolved in a sufficient amount of injection solvent for a targeted concentration of API of about 600 micrograms/mL.

1.60 Method 1, or any of 1.1 et seq., wherein the method further comprises comparing the retention time of one or more peaks eluting from the column with the retention time of one or more reference standards (e.g., the API) under substantially identical elution conditions.

1.61 Method 1.60, wherein the reference standard is cyclosporin A dissolved in about 50:50 v/v water-acetonitrile at a concentration of 3 to 800 micrograms/ml, e.g., about 6 micrograms/mL (or 4, 5, 7 or 8 micrograms/mL) and/or 600 micrograms/mL (or 300, 400, 500, 700 or 800 micrograms/mL).

1.62 Method 1.60 or 1.61, wherein the API from the injection sample elutes at a retention time of not more than 5% earlier or later than the retention time of the API from the reference standard.

1.63 Method 1.60, 1.61 or 1.62, wherein the peak symmetry factor of the one or more reference standards for the API is between 0.8 and 1.5.

In a second aspect, the present disclosure provides a method (Method 2) of determining the contents of a liquid pharmaceutical composition comprising a semifluorinated alkane (SFA) vehicle, e.g., determining the content of the API, the SFA, any excipients or solvents, and/or any impurities. In further embodiments of the second aspect, the present disclosure provides:

2.1 Method 2, wherein the pharmaceutical composition comprises the API dissolved, dispersed or suspended in a liquid vehicle comprising the SFA (e.g., at least one SFA).

2.2 Method 2.1, wherein the liquid vehicle comprises at least 50% v/v of the SFA, e.g., at least 60% v/v, or at least 70% v/v, or at least 80% v/v, or at least 85% v/v, or at least 90% v/v, or at least 95% v/v, or at least 96% v/v, or at least 97% v/v, or at least 98% v/v, or at least 99% v/v, of the SFA.

2.3 Method 2.1 or 2.2, wherein the liquid vehicle further comprises a non-SFA co-solvent (e.g., ethanol).

2.4 Method 2.3, wherein the liquid vehicle comprises the non-SFA co-solvent (e.g., ethanol) in an amount of not more than 5% v/v, e.g., 0.1-2% v/v or 0.5-1.5% or about 1% v/v.

2.5 Method 2, or any of 2.1-2.4, wherein the liquid vehicle comprises a second SFA that is different than the first SFA, optionally with a non-SFA co-solvent.

2.6 Method 2.5, wherein the second SFA is a structural isomer of the first SFA.

2.7 Method 2.5 or 2.6, wherein the vehicle consists of a first SFA, optionally a second SFA, and optionally a non-SFA co-solvent.

2.8 Method 2.7, wherein the vehicle consists of a first SFA, a second SFA which is a structural isomer of the first SFA, and ethanol.

2.9 Method 2.7 or 2.8, wherein the vehicle consists of at least 97% v/v of the first SFA and not more than 1% v/v of the second SFA and not more than 2% v/v of the non-SFA cosolvent (e.g., ethanol), e.g., at least 98% v/v of the first SFA and not more than 0.5% v/v of the second SFA and not more than 1% v/v of the non-SFA cosolvent (e.g., ethanol).

2.10 Method 2.7, wherein the vehicle consists of at least 99% v/v of the first SFA and not more than 0.5% v/v of the second SFA and no non-SFA cosolvent (e.g., no ethanol).

2.11 Method 2, or any of 2.1 et seq., wherein method comprises an analytical step of reverse-phase high-pressure liquid chromatography (RP-HPLC).

2.12 Method 2 or any of 2.1 et seq., wherein the method comprises the step of removing a portion of (e.g., all or substantially all) of the liquid vehicle of the composition before submission to RP-HPLC analysis (e.g., before injection onto the RP-HPLC column).

2.13 Method 2.12, wherein at least 50% of the volume of the liquid vehicle is removed, e.g., at least 60%, or at least 70%, or at least 80%, or at least 90%, or at least 95%, or at least 97% or at least 99.

2.14 Method 2.12 or 2.13, wherein the removal step comprises evaporation of the liquid vehicle, optionally under vacuum and/or under elevated temperature (e.g., >30° C.).

2.15 Method 2 or any of 2.1 et seq, wherein the method comprises the steps of:

a. Taking a representative sample of the pharmaceutical composition;

b. Removing a portion of the liquid vehicle from the pharmaceutical composition, e.g., by evaporation to yield a residue;

c. Dissolving the residue in a suitable injection solvent to form the injection sample;

d. Causing the injection sample to be introduced onto a reverse-phase high-pressure liquid chromatography (HPLC) column comprising a stationary phase;

e. Causing a liquid mobile phase to un through the column in order to separate and elute the components of the pharmaceutical composition;

f. Detecting the components eluting off the column, e.g., using at least ultraviolet detection;

g. Identifying the components of and/or determining the purity of the pharmaceutical composition.

2.16 Method 2, or any of 2.1 et seq., wherein the components determined are selected from the API (e.g., cyclosporin A), impurities derived from or related to the API (e.g., isocyclosporin A, cyclosporin C, cyclosporin B, cyclosporin D, cyclosporin U, cyclosporin H, dihydrocyclosporin A), the solvents (e.g., 1-perfluorobutylpentane or 1-perfluorohexyloctane, or ethanol), or any other components or excipients known or expected to be comprised in the pharmaceutical composition (e.g., 2-perfluorobutylpentane or 2-perfluorohexyloctane) such as leachable organic compounds, or any combination thereof, preferably wherein the components determined are selected from the API (e.g., cyclosporin A), impurities derived from or related to the API (e.g., isocyclosporin A, cyclosporin C, cyclosporin B, cyclosporin D, cyclosporin U, cyclosporin H, dihydrocyclosporin A), or any leachable organic compounds (e.g., 1-hydroxy-cyclohexyl phenyl ketone, 9,9-bis(methoxymethyl)-9H-fluorene (BMMF), 3,3',3-,5,5',5'-hexa-tert-butyl-alpha,alpha',alpha"-(mesitylene-2,4,6-triyl)-tri-p-cresol).

2.17 Method 2, or any of 2.1 et seq., wherein the pharmaceutical composition comprises at least 25% by weight of the SFA, e.g., at least 50% by weight, or at least 75% by weight, or at least 80% by weight, or at least 85% by weight, or at least 90% by weight, of the SFA.

2.18 Method 2, or any of 2.1 et seq., wherein the pharmaceutical composition comprises at least 95% by weight of the SFA, e.g., at least 97% or at least 98% or at least 99%, by weight, of the SFA.

2.19 Method 2, or any of 2.1 et seq., wherein the API is selected from cyclosporin, tacrolimus, sirolimus, and everolimus, e.g., the API is cyclosporin A.

2.20 Method 2, or any of 2.1 et seq., wherein the pharmaceutical composition consists essentially of cyclosporin A and the SFA.

2.21 Method 2.20, wherein the pharmaceutical composition consists of cyclosporin A and the SFA.

2.22 Method 2, or any of 2.1 et seq., wherein the SFA has the general formula RFRH, wherein RF represents a perfluoroalkyl segment having 2 to 10 carbon atoms, and RH represents a non-fluorinated alkyl segment having 2 to 12 carbon atoms.

2.23 Method 2, or any of 2.1 et seq., wherein the SFA is selected from the group consisting of F2H4, F4H5, F6H2, F6H6, and F6H8.

2.24 Method 2, or any of 2.1 et seq., wherein the SFA is F4H5 (1-perfluorobutylpentane).

2.25 Method 2, or any of 2.1 et seq., wherein the composition (e.g., the vehicle) comprises a single SFA (e.g., F4H5).

2.26 Method 2, or any of 2.1 et seq., wherein the composition (e.g., the vehicle) comprises a first SFA and second SFA (i.e., which are different SFAs) (e.g., wherein at least one is F4H5).

2.27 Method 2.26, wherein the second SFA is a structural isomer of the first SFA (e.g., one SFA is linear and the other SFA is branched, but both SFAs have the same chemical formula).

2.28 Method 2.27, wherein the first SFA is 1-perfluorobutylpentane and the second SFA is 2-perfluorobutylpentane.

2.29 Method 2.26, 2.27 or 2.28, wherein the composition comprises at least 75% by weight of the first SFA and not more than 25% by weight of the second SFA, for example, at least 80% by weight of the first SFA and not more than 20% by weight of the second SFA, or at least 85% by weight of the first SFA and not more than 15% by weight of the second SFA, or at least 90% by weight of the first SFA and not more than 10% by weight of the second SFA, or at least 95% by weight of the first SFA and not more than 5% by weight of the second SFA, or at least 97% by weight of the first SFA and not more than 3% by weight of the second SFA, or at least 98% by weight of the first SFA and not more than 2% by weight of the second SFA (e.g. 0.2%, or 0.4%, or 0.6%, or 0.8%, or 1.0%, 1.2%, or 1.4%, or 1.6%, or 1.8%, or 2.0% of the second SFA), or at least 97% by weight of the first SFA and not more than 1% by weight of the second SFA (e.g. 0.2%, or 0.4%, or 0.6%, or 0.8%, or 1.0% of the second SFA, or at least 97% by weight of the first SFA and not more than 0.5% by weight of the second SFA (e.g. 0.2%, or 0.3%, or 0.4%, or 0.5% of the second SFA), or at least 97% by weight of the first SFA and not more than 0.4% by weight of the second SFA (e.g., 0.2%, or 0.3% or 0.4% of the second SFA).

2.30 Method 2, or any of 2.1 et seq., wherein the composition does not comprise any excipients or co-solvents.

2.31 Method 2, or any of 2.1 et seq., wherein the composition comprises up to 1.0 wt. % of ethanol as co-solvent.

2.32 Method 2 or any of 2.1 et seq., wherein the pharmaceutical composition consists essentially of cyclosporin A, the SFA (e.g., F4H5) and ethanol.

2.33 Method 2 or any of 2.1 et seq., wherein the pharmaceutical composition consists of cyclosporin A the SFA (e.g., F4H5) and ethanol.

2.34 Method 2, or any of 2.1 et seq., wherein the composition comprises from 0.01 to 1.1% w/v of the API (e.g., cyclosporin), e.g., about 1.0% w/v.

2.35 Method 2, or any of 2.1 et seq., wherein the composition comprises from 0.01 to 0.55% w/v of the API (e.g., cyclosporin), e.g., about 0.5% w/v.

2.36 Method 2, or any of 2.1 et seq., wherein the composition comprises from 0.01 to 0.15% w/v of the API (e.g., cyclosporin), e.g., about 0.10% w/v.

2.37 Method 2, or any of 2.1 et seq., wherein the composition comprises from 0.01 to 0.06% w/v of the API (e.g., cyclosporin), e.g., about 0.05% w/v.

2.38 Method 2, or any of 2.1 et seq., wherein the composition comprises or essentially consists of 0.05-0.10% (w/v) cyclosporin A, dissolved in 1-perfluorobutylpentane and up to about 1 wt. % ethanol.

2.39 Method 2, or any of 2.1 et seq., wherein the composition comprises or essentially consists of 0.05% (w/v) cyclosporin A, dissolved in 1-perfluorobutylpentane and up to about 1 wt. % ethanol.

2.40 Method 2, or any of 2.1 et seq., wherein the composition comprises or essentially consists of 0.10% (w/v) cyclosporin A, dissolved in 1-perfluorobutylpentane and up to about 1 wt. % ethanol.

2.41 Method 2, or any of 2.1 et seq., wherein the composition comprises or essentially consists of 0.10% (w/v) cyclosporine A, not less than 97% wt. % F4H5, not more than 0.5 wt. % 2-perfluorobutylpentane, and up to about 1 wt. % ethanol, wherein the cyclosporine A is dissolved to form a solution (e.g., a clear solution).

2.42 Method 2, or any of 2.1 et seq., wherein the composition comprises or essentially consists of 0.10% (w/v) cyclosporine A, not less than 97% wt. % F4H5, not more than 0.5 wt. % 2-perfluorobutylpentane, with no co-solvent (e.g., no ethanol), wherein the cyclosporine A is dissolved to form a solution (e.g., a clear solution).

2.43 Method 2, or any of 2.1 et seq., wherein the composition comprises or essentially consists of 0.05% (w/v) cyclosporine A, not less than 97% wt. % F4H5, not more than 0.5 wt. % 2-perfluorobutylpentane, and up to about 1 wt. % ethanol, wherein the cyclosporine A is dissolved to form a solution (e.g., a clear solution).

2.44 Method 2, or any of 2.1 et seq., wherein the composition comprises or essentially consists of 0.05% (w/v) cyclosporine A, not less than 97% wt. % F4H5, not more than 0.5 wt. % 2-perfluorobutylpentane, with no co-solvent (e.g., no ethanol), wherein the cyclosporine A is dissolved to form a solution (e.g., a clear solution).

2.45 Method 2, or any of 2.1 et seq., wherein the composition is formulated for and/or approved for use as a topical ophthalmic eye drop.

2.46 Method 2.45, wherein the composition is formulated for and/or approved for application to the surface of the cornea and/or the conjunctiva.

2.47 Method 2.45 or 2.46, wherein the composition is formulated for and/or approved for use at a dosage of a single drop in each eye one to four times per day, e.g., once, twice or three times per day, e.g., for use at a dosage of a single drop in each eye two times per day.

2.48 Method 2.47, wherein the drop volume is 8 to 11 μL, or 8 to 10 μL, or about 10 μL.

2.49 Method 2.46, 2.47, 2.48 or 2.49, wherein the composition is formulated for and/or approved for the treatment of keratoconjunctivitis sicca (dry eye disease) or the signs and symptoms of keratoconjunctivitis sicca (dry eye disease), meibomian gland dysfunction (MGD), blepharitis, ocular surface damage, uveitis, ocular allergy, ocular neovascularization, intraocular inflammatory disease, or any symptoms associated with the foregoing.

2.50 Method 2, or any of 2.1 et seq., wherein the injection solvent of step (c) is water-acetonitrile mixture, e.g., about a 50:50 v/v mixture.

2.51 Method 2, or any of 2.1 et seq., wherein the mobile phase of step (e) comprises an elution gradient of a water-acetonitrile mixture, e.g., a gradient running from about 65% water/35% acetonitrile to about 35% water/65% acetonitrile (or a gradient running from about 65% water/35% acetonitrile to about 40% water/60% acetonitrile), followed by a column purge to return to initial conditions (e.g., a ten-minute purge with 65% water/35% acetonitrile, or a ten minutes purge with 10% water/90% acetonitrile followed by a ten-minute purge with 65% water/35% acetonitrile), optionally wherein the mobile phase further comprises about 0.05-0.10% v/v of an acid, e.g., phosphoric acid.

2.52 Method 2, or any of 2.1 et seq., wherein the stationary phase of the column of step (d) is a modified silica, e.g., high-purity porous silica having chemically bonded surface groups (e.g., isopropyl and/or nitrile groups).

2.53 Method 2.52, wherein the stationary phase of the column of step (d) is high-purity porous silica having chemically bonded nitrile groups, e.g., a stationary phase conforming to U.S. Pharmacopeia Method L10 (such as the Agilent SB-CN column series).

2.54 Method 2, or any of 2.1 et seq., wherein detection of step (f) is performed using a wavelength of 180 to 230 nm (e.g., 210 nm wavelength).

2.55 Method 2, or any of 2.1 et seq., wherein step (b) is performed by subjecting the sample to a stream of a gas, such as an inert gas, e.g., nitrogen or argon, to evaporate the vehicle (e.g., the SFA, e.g., F4H5).

2.56 Method 2, or any of 2.1 et seq., wherein step (b) is performed by vacuum evaporation, e.g., by subjecting the sample to a reduced pressure (e.g., a pressure below the vapor pressure of the vehicle), such to evaporate or support the evaporation of the vehicle (e.g., the SFA, e.g., F4H5)

2.57 Method 2.55 or 2.56, wherein the evaporation takes place at 25-50° C. (e.g., about 30° C.), for 30 to 500 minutes (e.g., at least 60 minutes).

2.58 Method 2, or any of 2.1 et seq., wherein:

a. The stationary phase of the column has particles having an average particle size diameter of 1-10 microns, or 1.5-10 microns, or 1.8-10 microns, or 3 to 10 microns, e.g., 1.8, or 3.5 or 5 microns; and/or b. The stationary phase of the column has particles having an average pore size of 50 to 500 Angstroms, e.g., 250 to 500 Angstroms, or 150 to 450 Angstroms, or 250 to 350 Angstroms, about 300 Angstroms, or about 80 Angstroms; and/or c. The mobile phases comprise about 0.08% v/v of 85% phosphoric acid; and/or d. The injection sample volume is about 20 microliters; and/or e. The mobile phase flow rate is about 1 mL/minute; and/or f. The column has a length of packed stationary phase of 15 to 250 mm, e.g., 250 mm; and/or g. The representative sample of the pharmaceutical composition is about 600 microliters, and the residue is redissolved in a sufficient amount of injection solvent for a targeted concentration of API of about 200 to 1000 micrograms/mL, or of about 400 to 800 micrograms/mL, e.g., 600 micrograms/mL.

2.59 Method 2, or any of 2.1 et seq., wherein the method further comprises comparing the retention time of one or more peaks eluting from the column with the retention time of one or more reference standards (e.g., the API) under substantially identical elution conditions.

2.60 Method 2.59, wherein the reference standard is cyclosporin A dissolved in about 50:50 v/v water-acetonitrile at a concentration of about 3 to 800 micrograms/ml, e.g., 6 micrograms/mL (or 4, 5, 7 or 8 micrograms/mL) and/or 600 micrograms/mL (or 300, 400, 500, 700 or 800 micrograms/mL).

2.61 Method 2.59 or 2.60, wherein the API from the injection sample elutes at a retention time of not more than 5% earlier or later than the retention time of the API from the reference standard.

2.62 Method 2.59, 2.60 or 2.61, wherein the peak symmetry factor of the one or more reference standards for the API is between 0.8 and 1.5.

In a third aspect, the present disclosure provides a method (Method 3) of manufacturing a liquid pharmaceutical composition comprising an active pharmaceutical ingredient (API) dissolved, suspended or dispersed in a semifluorinated alkane (SFA) as the solvent for the API, wherein the method comprises the step of determining the content of the API in a lot sample of the composition according to Method 1, or any of 1.1 et seq., or the step of determining the contents of the pharmaceutical composition according to Method 2, or any of 2.1 et seq. In further embodiments of the third aspect, the present disclosure provides:

3.1 Method 3, wherein the pharmaceutical composition comprises the API dissolved, dispersed or suspended in a liquid vehicle comprising the SFA (e.g., at least one SFA).

3.2 Method 3.1, wherein the liquid vehicle comprises at least 50% v/v of the SFA, e.g., at least 60% v/v, or at least 70% v/v, or at least 80% v/v, or at least 85% v/v, or at least 90% v/v, or at least 95% v/v, or at least 96% v/v, or at least 97% v/v, or at least 98% v/v, or at least 99% v/v, of the SFA.

3.3 Method 3.1 or 3.2, wherein the liquid vehicle further comprises a non-SFA co-solvent (e.g., ethanol).

3.4 Method 3.3, wherein the liquid vehicle comprises the non-SFA co-solvent (e.g., ethanol) in an amount of not more than 5% v/v, e.g., 0.1-2% v/v or 0.5-1.5% or about 1% v/v.

3.5 Method 3, or any of 3.1-3.4, wherein the liquid vehicle comprises a second SFA that is different than the first SFA, optionally with a non-SFA co-solvent.

3.6 Method 3.5, wherein the second SFA is a structural isomer of the first SFA.

3.7 Method 3.5 or 3.6, wherein the vehicle consists of a first SFA, optionally a second SFA, and optionally a non-SFA co-solvent.

3.8 Method 3.7, wherein the vehicle consists of a first SFA, a second SFA which is a structural isomer of the first SFA, and ethanol.

3.9 Method 3.7 or 3.8, wherein the vehicle consists of at least 97% v/v of the first SFA and not more than 1% v/v of the second SFA and not more than 2% v/v of the non-SFA cosolvent (e.g., ethanol), e.g., at least 98% v/v of the first SFA and not more than 0.5% v/v of the second SFA and not more than 1% v/v of the non-SFA cosolvent (e.g., ethanol).

3.10 Method 3.7, wherein the vehicle consists of at least 99% v/v of the first SFA and not more than 0.5% v/v of the second SFA and no non-SFA cosolvent (e.g., no ethanol).

3.11 Method 3, or any of 3.1 et seq., wherein the method comprises the steps of:
- a. Dissolving, suspending or dispersing the API in the SFA;
- b. Optionally, adding any other pharmaceutically acceptable solvents (e.g., non-SFA cosolvent such as ethanol, or additional SFA solvents) or excipients;
- c. Sterilizing and/or packaging the composition for distribution; and
- d. Analyzing a lot sample of the composition for the content of the API according to Method 1, or any of 1.1 et seq. and/or or the step of determining the contents of the pharmaceutical composition according to Method 2, or any of 2.1 et seq.

3.12 Method 3, or any of 3.1 et seq., wherein the pharmaceutical composition comprises at least 25% by weight of the SFA, e.g., at least 50% by weight, or at least 75% by weight, or at least 80% by weight, or at least 85% by weight, or at least 90% by weight, of the SFA.

3.13 Method 3, or any of 3.1 et seq., wherein the pharmaceutical composition comprises at least 95% by weight of the SFA, e.g., at least 97% or at least 98% or at least 99%, by weight of the SFA.

3.14 Method 3, or any of 3.1 et seq., wherein the API is selected from cyclosporin, tacrolimus, sirolimus, and everolimus, e.g., the API is cyclosporin A.

3.15 Method 3, or any of 3.1 et seq., wherein step (b) is omitted, and wherein the pharmaceutical composition consists essentially of cyclosporin A and the SFA.

3.16 Method 3.15, wherein the pharmaceutical composition consists of cyclosporin A and the SFA.

3.17 Method 3, or any of 3.1 et seq., wherein the SFA has the general formula RFRH, wherein RF represents a perfluoroalkyl segment having 2 to 10 carbon atoms, and RH represents a non-fluorinated alkyl segment having 2 to 12 carbon atoms.

3.18 Method 3, or any of 3.1 et seq., wherein the SFA is selected from the group consisting of F2H4, F4H5, F6H2, F6H6, and F6H8.

3.19 Method 3, or any of 3.1 et seq., wherein the SFA is F4H5 (1-perfluorobutylpentane).

3.20 Method 3, or any of 3.1 et seq., wherein the composition (e.g., the vehicle) comprises a single SFA (e.g., F4H5).

3.21 Method 3, or any of 3.1 et seq., wherein the composition (e.g., the vehicle) comprises a first SFA and second SFA (i.e., which are different SFAs) (e.g., wherein at least one is F4H5).

3.22 Method 3.21, wherein the second SFA is a structural isomer of the first SFA (e.g., one SFA is linear and the other SFA is branched, but both SFAs have the same chemical formula).

3.23 Method 3.22, wherein the first SFA is 1-perfluorobutylpentane and the second SFA is 2-perfluorobutylpentane.

3.24 Method 3.21, 3.22 or 3.23 wherein the composition comprises at least 75% by weight of the first SFA and not more than 25% by weight of the second SFA, for example, at least 80% by weight of the first SFA and not more than 20% by weight of the second SFA, or at least 85% by weight of the first SFA and not more than 15% by weight of the second SFA, or at least 90% by weight of the first SFA and not more than 10% by weight of the second SFA, or at least 95% by weight of the first SFA and not more than 5% by weight of the second SFA, or at least 97% by weight of the first SFA and not more than 3% by weight of the second SFA, or at least 98% by weight of the first SFA and not more than 2% by weight of the second SFA (e.g. 0.2%, or 0.4%, or 0.6%, or 0.8%, or 1.0%, or 1.2%, or 1.4%, or 1.6%, or 1.8%, or 2.0% of the second SFA), or at least 97% by weight of the first SFA and not more than 1% by weight of the second SFA (e.g. 0.2%, or 0.4%, or 0.6%, or 0.8%, or 1.0% of the second SFA, or at least 97% by weight of the first SFA and not more than 0.5% by weight of the second SFA (e.g. 0.2%, or 0.3%, or 0.4%, or 0.5% of the second SFA), or at least 97% by weight of the first SFA and not more than 0.4% by weight of the second SFA (e.g., 0.2%, or 0.3% or 0.4% of the second SFA).

3.25 Method 3, or any of 3.1 et seq., wherein step (b) is omitted and the composition does not comprise any excipients or co-solvents.

3.26 Method 3, or any of 3.1 et seq., wherein step (b) comprises the addition of ethanol, e.g., such that the composition comprises up to 1.0 wt. % of ethanol as co-solvent.

3.27 Method 3 or any of 3.1 et seq., wherein the pharmaceutical composition consists essentially of cyclosporin A, the SFA and ethanol.

3.28 Method 3 or any of 3.1 et seq., wherein the pharmaceutical composition consists of cyclosporin A the SFA and ethanol.

3.29 Method 3, or any of 3.1 et seq., wherein the composition comprises from 0.01 to 1.1% w/v of the API (e.g., cyclosporin), e.g., about 1.0% w/v.

3.30 Method 3, or any of 3.1 et seq., wherein the composition comprises from 0.01 to 0.55% w/v of the API (e.g., cyclosporin), e.g., about 0.5% w/v.

3.31 Method 3, or any of 3.1 et seq., wherein the composition comprises from 0.01 to 0.15% w/v of the API (e.g., cyclosporin), e.g., about 0.10% w/v.

3.32 Method 3, or any of 3.1 et seq., wherein the composition comprises from 0.01 to 0.06% w/v of the API (e.g., cyclosporin), e.g., about 0.05% w/v.

3.33 Method 3, or any of 3.1 et seq., wherein the composition comprises or essentially consists of 0.05-0.10% (w/v) cyclosporin A, dissolved in 1-perfluorobutylpentane and up to about 1 wt. % ethanol.

3.34 Method 3, or any of 3.1 et seq., wherein the composition comprises or essentially consists of 0.05% (w/v) cyclosporin A, dissolved in 1-perfluorobutylpentane and up to about 1 wt. % ethanol.

3.35 Method 3, or any of 3.1 et seq., wherein the composition comprises or essentially consists of 0.10% (w/v) cyclosporin A, dissolved in 1-perfluorobutylpentane and up to about 1 wt. % ethanol.

3.36 Method 3, or any of 3.1 et seq., wherein the composition comprises or essentially consists of 0.10% (w/v) cyclosporine A, not less than 97% wt. % F4H5, not more than 0.5 wt. % 2-perfluorobutylpentane, and up to about 1 wt. % ethanol, wherein the cyclosporine A is dissolved to form a solution (e.g., a clear solution).

3.37 Method 3, or any of 3.1 et seq., wherein the composition comprises or essentially consists of 0.10% (w/v) cyclosporine A, not less than 97% wt. % F4H5, not more than 0.5 wt. % 2-perfluorobutylpentane, with no co-solvent (e.g., no ethanol), wherein the cyclosporine A is dissolved to form a solution (e.g., a clear solution).

3.38 Method 3, or any of 3.1 et seq., wherein the composition comprises or essentially consists of 0.05% (w/v) cyclosporine A, not less than 97% wt. % F4H5, not more than 0.5 wt. % 2-perfluorobutylpentane, and up to about 1 wt. % ethanol, wherein the cyclosporine A is dissolved to form a solution (e.g., a clear solution).

3.39 Method 3, or any of 3.1 et seq., wherein the composition comprises or essentially consists of 0.05% (w/v) cyclosporine A, not less than 97% wt. % F4H5, not more than 0.5 wt. % 2-perfluorobutylpentane, with no co-solvent (e.g., no ethanol), wherein the cyclosporine A is dissolved to form a solution (e.g., a clear solution).

3.40 Method 3, or any of 3.1 et seq., wherein the composition is formulated for and/or approved for use as a topical ophthalmic eye drop.

3.41 Method 3.40, wherein the composition is formulated for and/or approved for application to the surface of the cornea and/or the conjunctiva.

3.42 Method 3.40 or 3.41, wherein the composition is formulated for and/or approved for use at a dosage of a single drop in each eye one to four times per day, e.g., once, twice or three times per day, e.g., for use at a dosage of a single drop in each eye two times per day.

3.43 Method 3.42, wherein the drop volume is 8 to 11 μL, or 8 to 10 μL, or about 10 μL.

3.44 Method 3.39, 3.40, 3.41 or 3.32, wherein the composition is formulated for and/or approved for the treatment of keratoconjunctivitis sicca (dry eye disease) or the signs and symptoms of keratoconjunctivitis sicca (dry eye disease), meibomian gland dysfunction (MGD), blepharitis, ocular surface damage, uveitis, ocular allergy, ocular neovascularization, intraocular inflammatory disease, or any symptoms associated with the foregoing.

3.45 Method 3, or any of 3.1 et seq., wherein the pharmaceutical composition consists of cyclosporin A dissolved in F4H5 at a concentration of about 0.05% w/v.

3.46 Method 3, or any of 3.1 et seq., wherein the pharmaceutical composition consists of cyclosporin A dissolved in F4H5 at a concentration of about 0.10% w/v.

It is understood that while the purpose of Method 1, et seq., is to determine the content of the API in the liquid pharmaceutical composition (commonly called "assaying"), the purpose of Method 2, et seq., is to determine all of the contents of the liquid pharmaceutical composition. The result of the Method 1 may be a determination of API content that is absolute (e.g., 0.1% w/v or 10 micrograms/mL) or as relative, such as a percent of the intended, calculated, or label API content (e.g., 98%). For example, if a liquid pharmaceutical composition is manufactured to have an API content of 10 micrograms/mL, and the Method 1 is carried out on a lot sample of the composition and makes a determination that the actual API content is 9.8 micrograms/mL, then such a lot would be considered to have an assay value of 98%. Typically, regulatory agencies require strict adherence to the intended API content of a pharmaceutical composition, and deviations of more than 5% are often not acceptable.

In contrast to Method 1, Method 2 evaluates the entire contents of a pharmaceutical composition, including the API, the solvent or vehicle, any excipients added, as well as any impurities present. Impurities may include impurities associated with the API, impurities associated with the solvent or vehicle, or even impurities associated with packaging or containers (such as leachable organic impurities). Impurities, particularly for API and solvents, may include side-products generated during synthesis, such as by-products or isomeric products, or impurities related to solvents or reagents used during synthesis. Regulatory agencies typically require all such impurities to be identifiable and their amounts tightly controlled in the final drug product.

The methods of the present disclosure may be applied to freshly or recently prepared batches of liquid pharmaceutical composition. This is often done as a routine quality control measure to ensure that product entering the marketplace meets the standards set by regulatory agencies. The methods of the present disclosure may also be applied to product that has been "aged." Aging studies are often performed under controlled experimental conditions in order to ensure that a pharmaceutical product will have an adequate shelf-life during which it remains safe and effective, for example, by showing that after 1-2 years, the API and other contents of the composition are substantially the same as when originally manufactured. Once a new pharmaceutical product enters the market place, actual product may be retrieved and tested according to methods disclosed herein to ensure that under actual distribution and storage conditions that the requisite standards for purity, safety and efficacy are being met. In addition, the present methods may be used in situations where a marketed product is suspected of being degraded, adulterated, or otherwise requiring testing to determine its contents.

Immunosuppressants are widely used to treat a variety of diseases and disorders. A subgroup of the immunosuppressant class of medications are the drugs which act on immunophilins as their mechanism of actions (as opposed to typical steroidal and non-steroidal anti-inflammatory medications). This class of drugs includes cyclosporin, tacrolimus, sirolimus, and everolimus.

Cyclosporine is as a pharmacological treatment for dry eye disease, which is available as a prescription medication, for example in the US in the form of an 0.05% ophthalmic (o/w) emulsion (Restasis®). This product is indicated to increase tear production in patients whose tear production is presumed to be suppressed due to ocular inflammation associated with keratoconjunctivitis sicca. Restasis® is administered twice a day in each eye approximately 12 hours apart. It is packaged in single-vials.

Cyclosporine (synonyms include cyclosporin A, CsA, or ciclosporin) is a cyclic non-ribosomal peptide comprising 11 amino acids with the empirical formula $C_{62}H_{111}N_{11}O_{12}$ and molecular weight of 1202.61 Da. It is an immunosuppressant drug that is widely used in post-allergenic organ transplant, to reduce the activity of the patient's immune system and thereby, the risk of organ rejection. Cyclosporine is typically provided as a colorless or white powder. Cyclosporine is thought to bind to the cytosolic protein cyclophilin (immunophilin) of immunocompetent lymphocytes, especially T-lymphocytes. This complex of cyclosporin and cyclophilin inhibits calcineurin, which, under normal circumstances, is responsible for activating the transcription of interleukin 2. It also inhibits lymphokine production and interleukin release and, therefore, leads to a reduced function of effector T-cells.

The pharmaceutical composition which is the subject of the present disclosure employs, as a liquid solvent (vehicle) for the API, an SFA, and optionally a co-solvent. Semifluorinated alkanes are linear or branched alkanes some of whose hydrogen atoms have been replaced by fluorine. The SFAs used in the present disclosure are composed of at least one non-fluorinated hydrocarbon segment and at least one perfluorinated hydrocarbon segment and are according to the general formula $F(CF_2)_n(CH_2)_mH$. Another nomenclature which may be used herein refers to the above-mentioned SFAs having two as RFRH, wherein RF designates a perfluorinated hydrocarbon segment, RH designates a non-fluorinated segment. Alternatively, the compounds may be referred to as FnHm, wherein F means a perfluorinated hydrocarbon segment, H means a non-fluorinated segment, and n, and m is the number of carbon atoms of the respective segment.

For example, F6H8 is used for 1-perfluorohexyloctane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

In some embodiments, the pharmaceutical composition which is the subject of the present disclosure uses an SFA solvent (vehicle) having the formula $F(CF_2)_n(CH_2)_mH$, in particular, SFAs of the formula $F(CF_2)_4(CH_2)_8H$ ($F_4H_5$), $F(CF_2)_4(CH_2)_8H$ ($F_4H_8$), $F(CF_2)_4(CH_2)_6H$ ($F_4H_6$), $F(CF_2)_6(CH_2)_6H$ ($F_6H_6$), $F(CF_2)_6(CH_2)_8H$ ($F_6H_8$), and $F(CF_2)_5(CH_2)_8H$ ($F_8H_8$).

In particular embodiments, the SFA is 1-perfluorobutylpentane, a semifluorinated alkane with the chemical formula $F(CF_2)_4(CH_2)_8H$. It is an inert, water-insoluble liquid, with a density of 1.295 g/cm$^3$ at 25° C. (±0.002 g/cm$^3$) and refractive index of 1.322 at 20° C. (±0.0015). Alternative nomenclature for this compound includes F4H5, wherein F denotes a linear perfluorinated alkane segment comprising 4 carbon atoms and wherein H denotes a linear and non-fluorinated alkane hydrocarbon segment of 5 carbon atoms. Preferably, the 1-perfluorobutyl-pentane is substantially free of water.

In some embodiments, the pharmaceutical composition which is the subject of the present disclosure may comprise a second SFA, in particular, a branched SFA. Thus, the composition may comprise a linear SFA and a branched SFA together, and in particular, the two SFAs may be structural isomers of each other. Thus, in some embodiments, the pharmaceutical composition which is the subject of the present disclosure comprises isomeric linear and branched SFA, such as, 1-perfluorobutylpentane and 2-perfluorobutylpentane (also known as perfluorobutyl-5-methylbutane or $CF_3(CF_2)_3$—$CH(CH_3)(CH_2)_2CH_3$). Generally, the linear SFA is the primary SFA, and the composition may optionally comprise minor amounts of the isomeric branched SFA, such as up to 2% (w/w), or up to 1% (w/w), or up to 0.5% (w/w), or up to 0.4% (w/w), or up to 0.3% (w/w) or up to 0.2% (w/w).

In some embodiments, the pharmaceutical composition which is the subject of the present disclosure may comprise up to about 1.0% (w/w) of ethanol as a co-solvent. In other embodiments, the compositions are essentially free of a co-solvent (such as ethanol), such as, where the composition consists essentially only of the API (e.g., cyclosporine) dissolved in the SFA (e.g., 1-perfluorobutyl-pentane).

As used herein, the term "up to about" or "up to" used in context of a parameter, such as presently in relation to the amount of ethanol in the composition, refers to any value of the parameter greater than zero and up to, and inclusive of, the defined parameter. For example, an amount of "up to about 1.0% (w/w) of ethanol" should be understood as including any value greater than zero ranging up to and including the value of 1.0% (w/w) of ethanol, and would include, for example, values such as 0.01%, 0.05%, 0.1%, 0.2%, 0.3%, 0.4%, 0.5% 0.6%, 0.7, 0.8, 0.9, 0.95%, 0.99% (w/w) of ethanol, taking into account any degree of variability usually observed in measuring or determining this parameter, using the standard techniques and equipment known in the relevant field.

The concentration of API (e.g., cyclosporin) in the pharmaceutical composition which is the subject of the present disclosure may be from 0.05 to 1.5% (w/v), such as about 0.1%, or about 0.5% or about 1.0%, (w/v) of the composition.

In particular embodiments, the present disclosure may pertain to compositions which comprise, or consist of:

(1) 0.1% (w/v) of cyclosporin dissolved in 1-perfluorobutyl-pentane and 0.5% (w/w) ethanol, or
(2) 0.1% (w/v) of cyclosporin dissolved in 1-perfluorobutyl-pentane and up to about 1% (w/w) ethanol, or
(3) 0.1% (w/v) cyclosporin dissolved in 1-perfluorobutyl-pentane and 1.0% (w/w) ethanol, or
(4) 0.1% (w/v) cyclosporin dissolved in 1-perfluorobutyl-pentane.

In particular further embodiments, the composition comprises a linear and a branched SFA isomers, such as, 1-perfluorobutylpentane and 2-perfluorobutylpentane. Accordingly, the present disclosure may pertain to compositions which comprise, or consist of:

(5) 0.1% (w/v) of cyclosporin dissolved in 1-perfluorobutyl-pentane and 0.5% (w/w) ethanol and up to 0.5 wt. % 2-perfluorobutylpentane, or
(6) 0.1% (w/v) of cyclosporin dissolved in 1-perfluorobutyl-pentane and up to about 1% (w/w) ethanol and up to 0.5 wt. % 2-perfluorobutylpentane, or
(7) 0.1% (w/v) cyclosporin dissolved in 1-perfluorobutyl-pentane and 1.0% (w/w) ethanol and up to 0.5 wt. % 2-perfluorobutylpentane, or
(8) 0.1% (w/v) cyclosporin dissolved in 1-perfluorobutyl-pentane and up to 0.5 wt. % 2-perfluorobutylpentane.

In particular further embodiments, the present disclosure may pertain to compositions which comprise, or consist of:

(9) 0.1% (w/v) cyclosporin A dissolved in not less than 97 wt. % F4H5 and up to about 1 wt. % ethanol and up to 0.5 wt. % 2-perfluorobutylpentane.

(10) 0.1% (w/v) cyclosporin A dissolved in not less than 97 wt. % F4H5 and up to 0.5 wt. % 2-perfluorobutylpentane.

(11) 0.05% (w/v) cyclosporin A dissolved in not less than 97 wt. % F4H5 and up to about 1 wt. % ethanol and up to 0.5 wt. % 2-perfluorobutylpentane.

(12) 0.05% (w/v) cyclosporin A dissolved in not less than 97 wt. % F4H5 and up to 0.5 wt. % 2-perfluorobutylpentane.

Unless otherwise indicated, the term "% (w/v)" denotes the amount of a component of a composition as a weight percentage in relation to the total volume of the composition (with 'w' denoting the weight and 'v' denoting volume). For example, 0.1% (w/v) would correspond to 1.0 mg of a component in 1 mL of the composition. Unless otherwise indicated, the term "% (w/w)" or wt. % refers to the amount of a component of a composition as a weight percentage in relation to the total weight of the composition (with 'w' denoting weight).

The term 'about' as used herein and in reference or connection to a parameter, for example such as the concentration of cyclosporine dissolved in the composition or the volume featured in a single dose or applied liquid drop of the composition includes the precise value as defined, as well as any value falling within the degree of variability usually observed in measuring or determining these parameters using the standard techniques and equipment known in the art and field.

The pharmaceutical compositions which are the subject of the present disclosure may be used for the treatment of human subjects with dry eye disease, as well as for any related conditions, or signs and symptoms associated therewith.

A dose of a composition as described in any one of the embodiments herein is topically administered in the form of a (i.e., one) single drop to an eye of a subject. The drop may be administered to the surface of the eye, preferably to any surface region or tissue of the eye that is accessible to topical administration or instillation, for example to the cornea or conjunctiva. The single drop of the composition may be instilled directly onto a surface of the eye, such as the corneal surface of the eye, or alternatively into a space, e.g., a sac or pocket formed by gently pulling down of the lower eyelid of an eye.

As used herein, the term 'administration to an eye' or 'per eye' refers to the administration of a given dose, e.g., a single dose, of a pharmaceutical composition according to the invention to an individual eye of a subject. The therapy of the dry eye disease and dry eye disease associated conditions as described herein however, should be understood as being not limited to the treatment of a single eye in a subject, but as being also inclusive of a therapy involving the administration of compositions according to the present invention to each, i.e., both eyes of a subject which are affected by the dry eye condition.

The pharmaceutical composition which is the subject of the present disclosure is preferably provided as a clear solution, wherein the API is fully dissolved and in solution in the SFA (at room temperature conditions (i.e., between 15 to 25° C.). In some embodiments, the compositions are provided in sterile form.

In another embodiment, the pharmaceutical composition which is the subject of the present disclosure is substantially free of water and/or substantially free of a preservative. As understood herein, the term 'substantially free', or alternatively 'essentially free' in reference to a composition constituent refers to the presence of said constituent in no more than trace amounts and that if present in trace amounts the constituent provides no technical contribution to the composition.

As used herein, the term "consists" and related terms "consisting" or "consist" is to be understood as meaning that no other features, other than those prefaced by the term are present.

In the context of pharmaceutical compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g., 'essentially consisting of").

The inventors of the present disclosure found that the pharmaceutical compositions, which are the subject of the present disclosure, cannot be reliably analyzed by traditional HPLC for assaying aqueous solutions. It was found that the SFA-containing, water-free pharmaceutical compositions of the present disclosure, when injected directly to the HPLC column, lead to highly unreliable and un-reproducible results. As unreliable, un-reproducible results pose a fundamental problem to regulatory approval for such a pharmaceutical composition, it was necessary to develop a reliable and reproducible method of assaying such a composition to determine its purity.

Upon investigation, the inventors surprisingly found that the SFA-containing, water-free pharmaceutical compositions of the present disclosure somehow negatively interact with the typical HPLC column material used in reverse-phase HPLC. Without being bound by theory, this was found surprising, as SFAs are readily miscible with acetonitrile (the organic part of the injection solvent). Surprisingly, the method of assaying the SFA-containing, water-free pharmaceutical compositions did produce reliable results, when the SFA was absent from the injection sample. This prompted the inventors to develop a method for removal of a portion or all of the SFA component from the pharmaceutical composition before injection of the sample to HPLC system.

Removal of the SFA from a sample of the pharmaceutical compositions, which are the subject of the present disclosure, may be performed by any method that is capable of removing a portion or all of the SFA contained in the sample to be analyzed, provided that the API (e.g., cyclosporine) is not degraded.

Removal of SFAs (e.g., 1-perflurobutylpentane and/or 2-perfluorobutylpentane) from samples of the pharmaceutical compositions, which are the subject of the present disclosure, is preferably performed by an evaporation technique. In a preferred embodiment, the sample may be subjected to a stream of gas (e.g., air), preferably an inert gas (e.g., nitrogen, argon) for removing a portion or all of the SFA from the sample. In this technique, a stream of gas is continuously blown over the surface of the composition, contained in an appropriate open vessel, such as a tube or vial, lowering the vapor pressure of the solvent as well as increasing the surface area, resulting in effective evaporation of the SFA from the sample. The gas to be utilized should be selected from a gas that does not cause the sample or the API (e.g., cyclosporine) contained in the sample to degrade. Air, nitrogen, argon, and other inert gases are suitable.

Alternatively, the removal of SFAs from samples of the pharmaceutical compositions, which are the subject of the present disclosure, may be performed using a vacuum evaporation technique. In this technique, the pressure is reduced below the vapor pressure of the SFA solvent, causing the SFA solvent to evaporate at a lower temperature than normal. Vacuum evaporation may be conducted at an elevated temperature, e.g., 30-60° C. Optionally, the removal of the SFAs from the samples may be conducted by applying lyophilization/freeze-drying techniques.

Preferably, the temperature during the evaporation is controlled, e.g., by a heat source or cooling source. The temperature is chosen to safeguard the integrity of the active ingredient while maximizing the efficiency of evaporation. Preferably, the evaporation is performed at 10-60° C., or at 15-50° C., or at 15-45° C., or at 20-40° C., or at ambient temperature.

Upon removal of a portion of the SFA from the sample, or all of the SFA from the sample, a residue, containing the API, is obtained, that can be dissolved in a suitable injection fluid to form the injection sample for subsequent HPLC analysis. By ensuring that the injection fluid is (essentially) free of the SFA solvent (or significantly reduced in content of the SFA solvent), the inventors were able to reliably and reproducibly assay the SFA-containing, water-free pharmaceutical compositions of the present disclosure.

For the reverse-phase HPLC described herein, the stationary phase is preferably a porous silica column, more preferably it is a column with chemically bonded functional groups (C18, C8, C4, Phenyl, CN), more preferably the stationary phase is functionalized, e.g., with isopropyl and/or nitrile groups, or the stationary phase comprises cyano groups (CN) that are chemically bonded to porous silica particles. In some embodiments, the stationary phase is compliant to U.S. Pharmacopeia Method L10 (such as by using the Agilent SB-CN column series).

The following examples serve to illustrate the invention of the present disclosure, however should not to be understood as restricting the scope of the invention.

EXAMPLES

Example 1. Experimental Method: Direct Injection

A sample of cyclosporin A is obtained, and is dissolved in 1-perfluorobutylpentane with 1 wt. % ethanol at concentrations of 0.5 mg/mL and 1.0 mg/mL. A reference sample of cyclosporin A in methanol at a concentration of 1.0 mg/mL is also obtained. Each sample is submitted to reverse-phase HPLC separation according to the following conditions:

Instrument: HPLC Alliance 2695, Waters
Detector. DAD at 210 nm wavelength
Column: Kinetex C18, 100 mm×4.6 mm
Flow rate: 1.5 mL/minute; run time: 30 minutes
Column Temperature: 80° C.; Autosampler temperature: 5° C.
Injection volume: 10 μL
Mobile Phase (A): Acetonitrile/Water/THF/TFA (45/50/5/0.05)
Mobile Phase (B): Acetonitrile/Water/Methanol/TFA (55/10/30/5/0.05)
Gradient: 0-5 minutes 95% (A); 5-20 minutes to 50% (A); 20-22 minutes 50% (A); 22-23 minutes 95% (A); 23-30 minutes 95% (A)

The retention time of the cyclosporin A in methanol solvent is found to be about 12.25 minutes. In contrast, the retention time of the cyclosporin A in 1-perfluorobutylpentane solvent with 1 wt. % ethanol is found to be shifted to about 10.5 minutes. The same retention time is obtained at both cyclosporin concentrations in 1-perfluorobutylpentane with 1 wt. % ethanol. The results are shown in FIG. 1.

It is further found, on additional experimental attempts, that the shift of the retention time of cyclosporin A in 1-perfluorobutyl pentane with 1 wt. % ethanol solvent is not reproducible (the retention time is variable), thus making the direct injection of cyclosporin in F4H5 solvent unsuitable for analytical use and quality control. It is further found that the selection of alternate mobile phase solvent systems and alternate stationary phase column systems does not result in improved performance. Without being bound by theory, it is believed that the semifluorinated alkane solvent (vehicle) disrupts the proper interaction between mobile phase and stationary phase in a reverse-phase HPLC column system. In particular, it is believed that gels form between the semifluorinated alkane and the silica of the stationary phase. This adverse interaction has not been previously reported.

Example 2. Experimental Method: Evaporation, Redissolution and Injection

The 0.5 mg/mL and 1.0 mg/mL cyclosporin A in 1-perfluorobutylpentane solutions with 1 wt. % ethanol of Example 1 are each evaporated under a stream of essentially 100% nitrogen gas (e.g., ultrapure nitrogen gas with >99% purity) at 30° C. in an autosampler vial. It is found that evaporation for 30 to 90 minutes, such as 60 minutes or more, results in a residue containing a minimal amount of remaining semifluorinated alkane solvent. It is further found that the residue is readily redissolved in 50:50 v/v water/acetonitrile mixture at a concentration of 0.5 mg/mL or 1.0 mg/mL.

Figure 2:
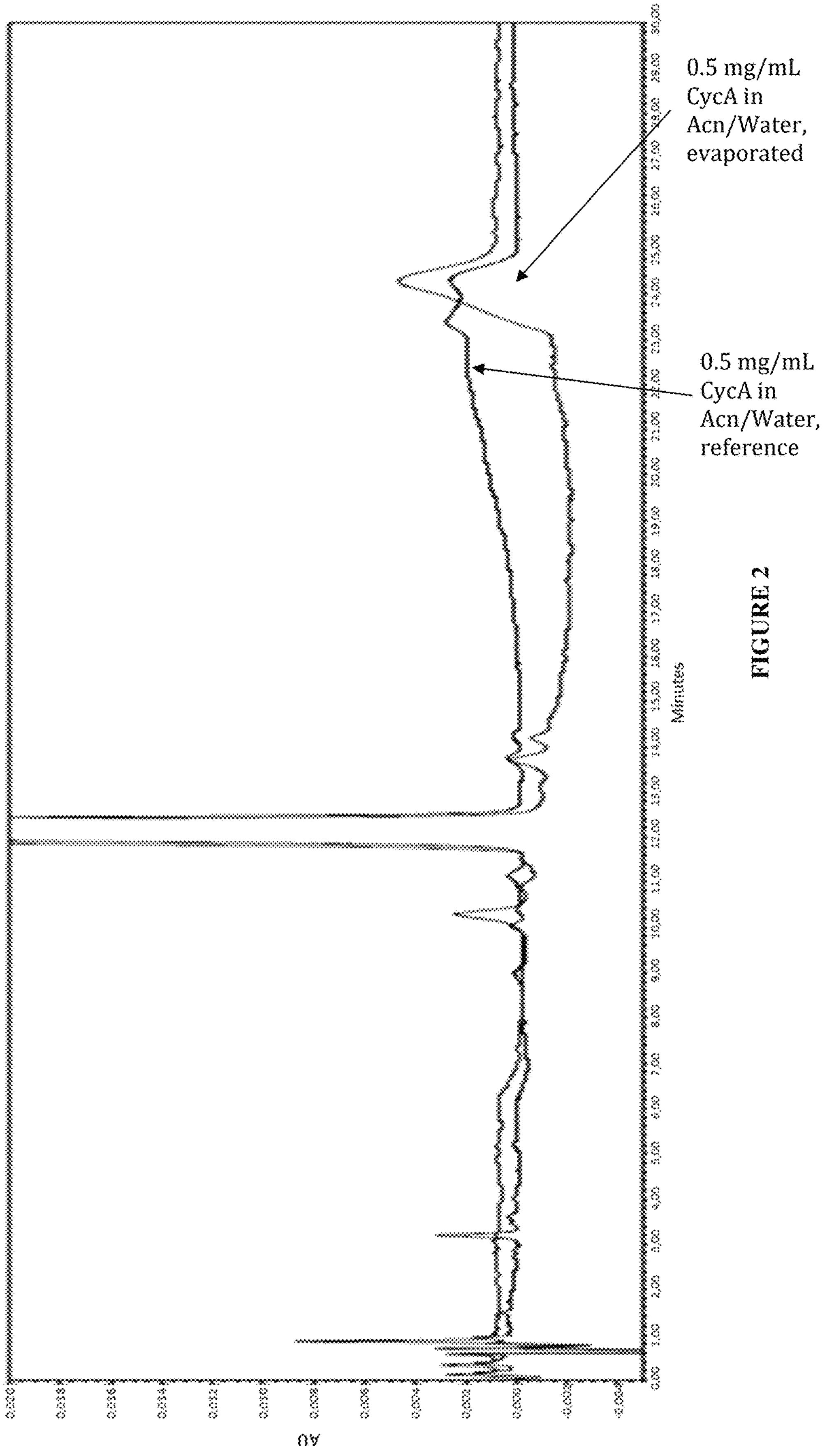
FIG. 2. HPLC chromatograms resulting from injection of redissolved residue of 0.5 mg/mL cyclosporin A (CycA) solutions in 50:50 v/v water/acetonitrile (Acn), in comparison to reference 0.5 mg/mL cyclosporin A in 50:50 v/v water/acetonitrile (Acn) (see Example 2).

The resulting redissolved 0.5 mg/mL sample of cyclosporin A in 50:50 v/v water/acetonitrile is submitted to HPLC under the conditions described in Example 1, along with a reference sample of cyclosporin A dissolved in 50:50 v/v water/acetonitrile at a concentration of 0.5 mg/mL. The results unexpectedly show that the cyclosporin A of both samples reliably elute with a retention time of 12.25 minutes. The results are shown in FIG. 2. Similar results are obtained for the 1.0 mg/mL redissolved cyclosporin A solution.

These results demonstrate that the evaporation of the semifluorinated alkane solvent (vehicle) of a pharmaceutical composition comprising cyclosporin A, such as by evaporating under a stream of gas, such as an inert gas (e.g., nitrogen), followed by redissolution of the sample in a suitable injection solvent, remedies the deleterious effects caused by the semi-fluorinated alkane solvent (vehicle).

Example 3. Analytical Method

Reference solutions are prepared for use in determining the purity of a commercial-ready lot of cyclosporin A in 1-perfluorobutylpentane (0.1% w/v) with 1 wt. % ethanol. Reference solution A is prepared in two separate batches (A-1 and A-2) by dissolving 15.0 mg of cyclosporin A reference material in 25.0 mL of 50:50 v/v water/acetonitrile ("Solvent"). Reference solution B is prepared in two batches (B-1 and B-2) by diluting 1.0 mL of reference solution A with additional Solvent to form a solution of 100.0 mL volume. Reference solution C is prepared by diluting 1.0 mL of reference solution B with additional Solvent to form a solution of 10.0 mL volume. System suitability solution (SSS) is prepared by dissolving 5.0 mg of cyclosporin A system suitability reference standard (European Pharmacopoeia Chemical Reference Standard, EP CRS) in 5.0 mL of Solvent (or dissolving 1.0 mg of cyclosporin A system suitability reference standard (EP CRS) in 1.0 mL of Solvent.)

The Vehicle Reference sample is 600 μL of 1-perfluorobutylpentane and 1 wt. % ethanol. The test samples are two separate batches of 600 μL samples from the same lot of 0.1% w/v cyclosporin A in 1-perfluorobutylpentane (test sample and test sample 2). The Vehicle Reference sample, test sample 1, and test sample 2 are each transferred into autosampler vials and evaporated under a stream of essentially 100% nitrogen gas (e.g., ultrapure nitrogen gas with >99% purity) for 30 to 90 minutes (e.g., 60 minutes), to yield the respective residues. The Vehicle Reference sample residue is then redissolved in 0.5 mL of Solvent. Each of the whitish test sample residues are also redissolved in 1.0 mL of Solvent. The resulting solutions are, respectively, Vehicle Reference Solution (VRS), Test Solution 1 and Test Solution 2.

Reverse-phase HPLC separation was carried out under the following conditions:

- Instrument: Agilent HPLC 1290 Series
- Detector: Agilent UV/Vis or DAD at 210 nm wavelength
- Column: Agilent SB-CN (high purity porous silica with bound nitrile groups (5 micron average particle size, 80 Angstrom pore size), 250 mm×4.6 mm
- Flow rate: 1.0 mL/minute; run time: 70 minutes
- Column Temperature: 75° C.; Autosampler temperature: 5° C.
- Injection volume: 20 μL
- Mobile Phase (A): water with 0.08% v/v of phosphoric acid, 85%
- Mobile Phase (B): acetonitrile with 0.08% v/v phosphoric acid, 85%
- Gradient: 0 minutes 65% (A); 0-55 minutes to 40% (A); 55-55.1 minutes to 65% (A); 55.1-65 minutes 65% (A)

Reverse-phase HPLC separation was conducted for. (A) Solvent, (B) SSS, (C) Reference Solution C, (D) Reference Solution B-1 (five sequential injections), (E) Reference Solution B-2, (F) Reference Solution A-1 (five sequential injections), (G) Reference solution A-2, (H) VRS solution, (I) Test Solution 1 (six sequential injections), (J) Test Solution 2 (six sequential injections, (K) Reference Solution A-1, (L) Reference Solution B-1, (M) Reference Solution C, (N) SSS, (O) Solvent.

System suitability is established by comparing the cyclosporin A peak areas obtained among the various reference sample injections. System suitability requires that the relative standard deviation of the peak areas of the five sequential injections of Reference Solution A-1 is less than or equal to 1.0%, and that the deviation of the peak area of Reference Solution A-2 peak is +/−1.5% of the average peak area of the five Reference Solution A-1 peak areas. This deviation is calculated as: Dev.=([Area Ref. A-2*Conc. Ref A-1]/[mean Area Ref. A-1*Conc. Ref A-2]*100)−100, where concentration is expressed in μg/mL. The same determinations and calculations are also applied to Reference Solution B-1 vis-A-vis Reference Solution B-2. Other acceptance criteria for the method are an RSD (n=5) of less than or equal to 2.0%, and a deviation between Reference Solution B-1 and Reference Solution B-2 of less than or equal to 3.0%.

As a further measure of the reliability of the analytical method, Peak Symmetry is determined. This is calculated using the symmetry factor, $A_S$, as follows: $A_S$=[width of peak at 1/20 peak height]/[2*D], wherein D is the distance between the perpendicular dropped from the peak maximum and the leading edge of the peak at 1/20 of the peak height. The peak symmetry factor must be between 0.8 and 1.5 for the cyclosporin peak in Reference Solution A and Reference Solution B.

As a further measure of the reliability of the analytical method, Peak to Valley ratio is determined. This is calculated as follows: P/V=[height above extrapolated baseline of minor peak]/[height above extrapolated baseline at lowest point of curve separating minor peak and major peak]. The P/V ratio between the neighboring peaks of the cyclosporin impurity U and the major cyclosporin A peak in the SSS must be at least 1.4 both at the first SSS injection (at sequence beginning) and at the second SSS injection (at sequence end).

As a further measure of the reliability of the analytical method, the signal-to-noise ratio for Reference Solution C is determined. This is calculated as follows: S/N=2*[Height of cyclosporin peak in Ref. Solution C]/[Height of background noise in Solvent solution chromatogram]. The S/N ratio of cyclosporin in the Reference Solution C chromatogram must be at least 10 at both, the first injection (at sequence beginning) and the second injection (at sequence end) of Reference Solution C.

As a further measure of the reliability of the analytical method, system drift (system stability) is determined. This is calculated by determination of the relative standard deviation of the before-sample and after-sample injections of Reference Solution A-1 and Reference Solution B-1, respectively. Matching/corresponding injection peak areas (of cyclosporin A) should not differ by more than 1.5% for Reference Solution A-1 and not more than 3.0% for Reference Solution B-1. Alternatively, the system stability can be determined by evaluation of the relative standard deviation of the peak areas of cyclosporin A in all reference solution A-1 injections in the sequence, which is not to exceed 1.5%; and by evaluation of the relative standard deviation of the peak areas of cyclosporin A in all reference solution B-1 injections in the sequence, which is not to exceed 3.0%.

If all of the above system suitability parameters are satisfactorily met, then the quantitative determination of the cyclosporin A content of the Test Solutions may be calculated. This is done by comparing the peak areas of the various peaks in the test solution chromatograms to the corresponding peaks in the reference solution chromatograms. These tests results may be calculated automatically by a computer program. The test results are reported as the mean of the two sample preparations (Test Solution 1 and Test Solution 2). The following equation is used: Assay (mg/mL)=$[A_S*D_S*TW_{RS}*\rho]/[A_{RS}*D_{RS}*W_S*0.001]$, wherein $A_S$ is peak area in the sample solution, $A_{RS}$ is the (corrected) mean peak area of the five-fold injections of Reference Solution A, $D_S$ is dilution of the sample solution (mL), $D_{RS}$ is dilution of the Reference Solution A (mL), $W_S$ is the weight of the sample (mg), $TW_{RS}$ is the corrected weight of the reference standard for Reference Solution A (mg), and ρ is the density of 1-perfluorobutylpentane at 25° C. (1.29 g/mL). The assay calculation provides a figure in mg/mL.

The purity of the Test Solution is determined by reference to the known and unknown impurities of cyclosporin A in Reference Solution B. Peaks in the Test Solution having an area below the corresponding peak area in Reference Solution C are not reported (or disregarded) because the concentration of Reference Solution C (0.1%) represents the reporting level for impurities or peak areas in the Test Solution are not reported or disregarded if their amount after quantification with Reference solution B equals NMT (not more than) 0.1%. Purity (%) is calculated using the following formula: Assay (%)=[$A_S$*$D_S$*$CW_{RS}$*ρ*100]/[$A_{RS}$*$D_{RS}$*$W_S$*TA], wherein TA is the target assay concentration (mg/mL) and the other values are as noted in preceding formula, except that $A_{RS}$ and $D_{RS}$ refer to Reference Solution B.

The known impurities of cyclosporin A are shown below based on their retention times in the HPLC method described in Example 3:

| | Retention Time (min) | Relative Retention Time |
|---|---|---|
| Cyclosporin A | 41.5 | 1 |
| Isocyclosporin A | 20.0 | 0.48 |
| Cyclosporin C | 36.5 | 0.88 |
| Cyclosporin B | 39.0 | 0.94 |
| Cyclosporin U | 41.1 | 0.99 |
| Cyclosporin H | 42.7 | 1.03 |
| Dihydrocyclosporin A | 43.5 | 1.05 |
| Cyclosporin D | 45.2 | 1.09 |

Figure 3A:
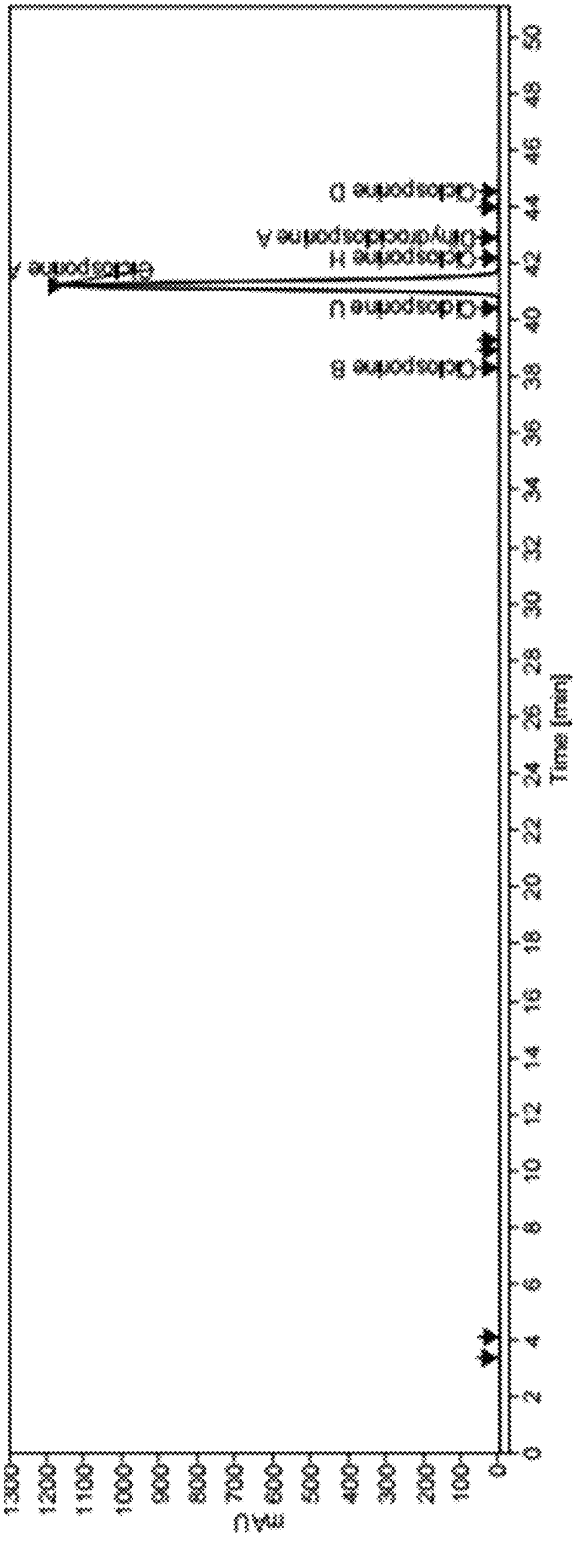
FIG. 3A. HPLC chromatogram of Reference Solution A of Example 3.
Figure 3B:
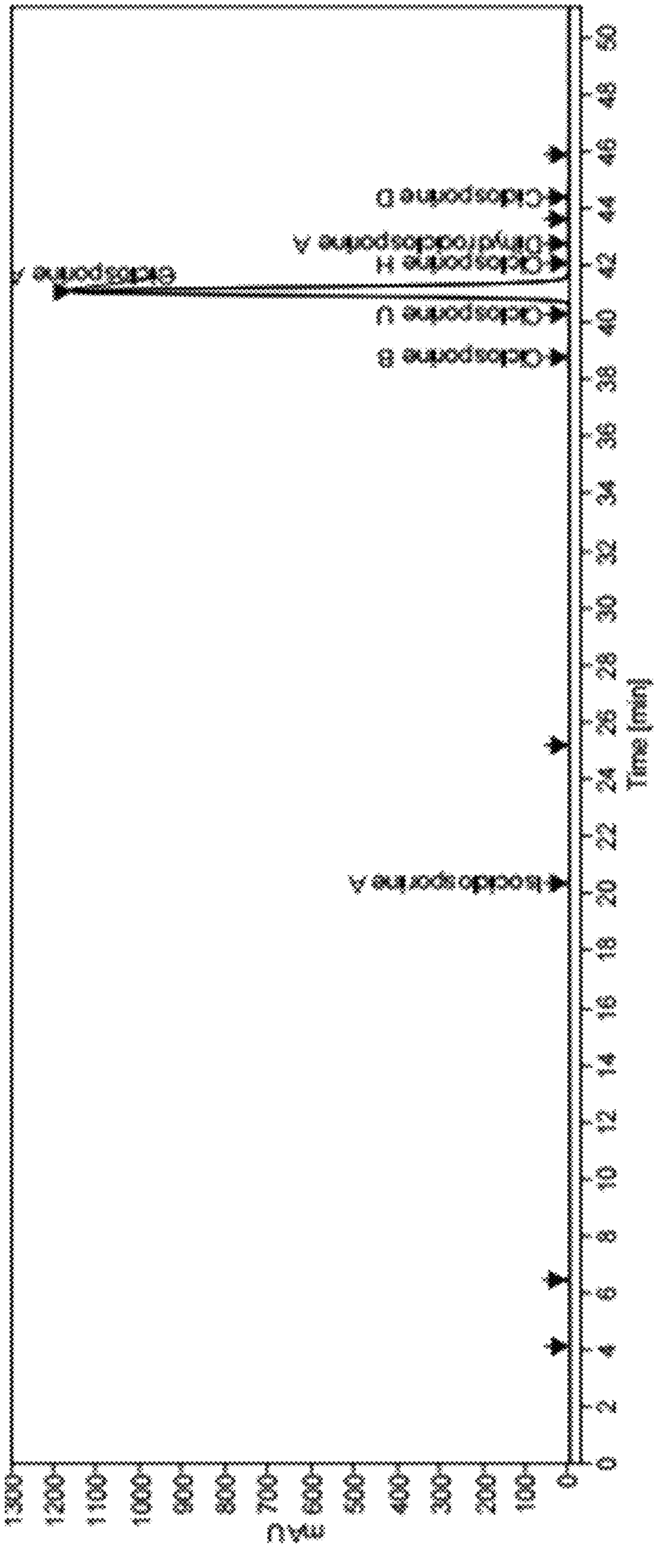
FIG. 3B. HPLC chromatogram of Test Solution 1 of Example 3.

FIG. 3A shows the HPLC chromatogram for Reference Solution A. FIG. 3B shows the HPLC chromatogram for Test Solution 1. These chromatograms demonstrate the efficacy of the test method. Further test runs are performed extensively, and these establish the reliability and repeatability of the analytical method, to result in a validated method.

The analytical method is also performed using a 0.05% cyclosporin A in 1-perfluorobutylpentane test sample following same procedure as above, except that in redissolving the evaporative residue in Solvent, 0.5 mL of Solvent is used instead of 1.0 mL Solvent (in order to achieve the same target concentration of 600 μg/mL).

Example 4. Analytical Method (Validated)

Further development and optimization of the analytical method results in modification of the gradient used in Example 3. After the 55-minute run time for eluting the relevant compounds from the column (a gradient from 65% A/35% B to 40% A/60% B), rather than a ten-minute column purge at 65% A/35% B, the column is purged for ten minutes at 10% A/90% B, followed by a ten-minute purge at 65% A/35% B. The conditions are otherwise as described in Example 3.

These changes provide improved system stability and reliability by more efficiently purging the column after each run to return it to initial conditions.

Figure 4:
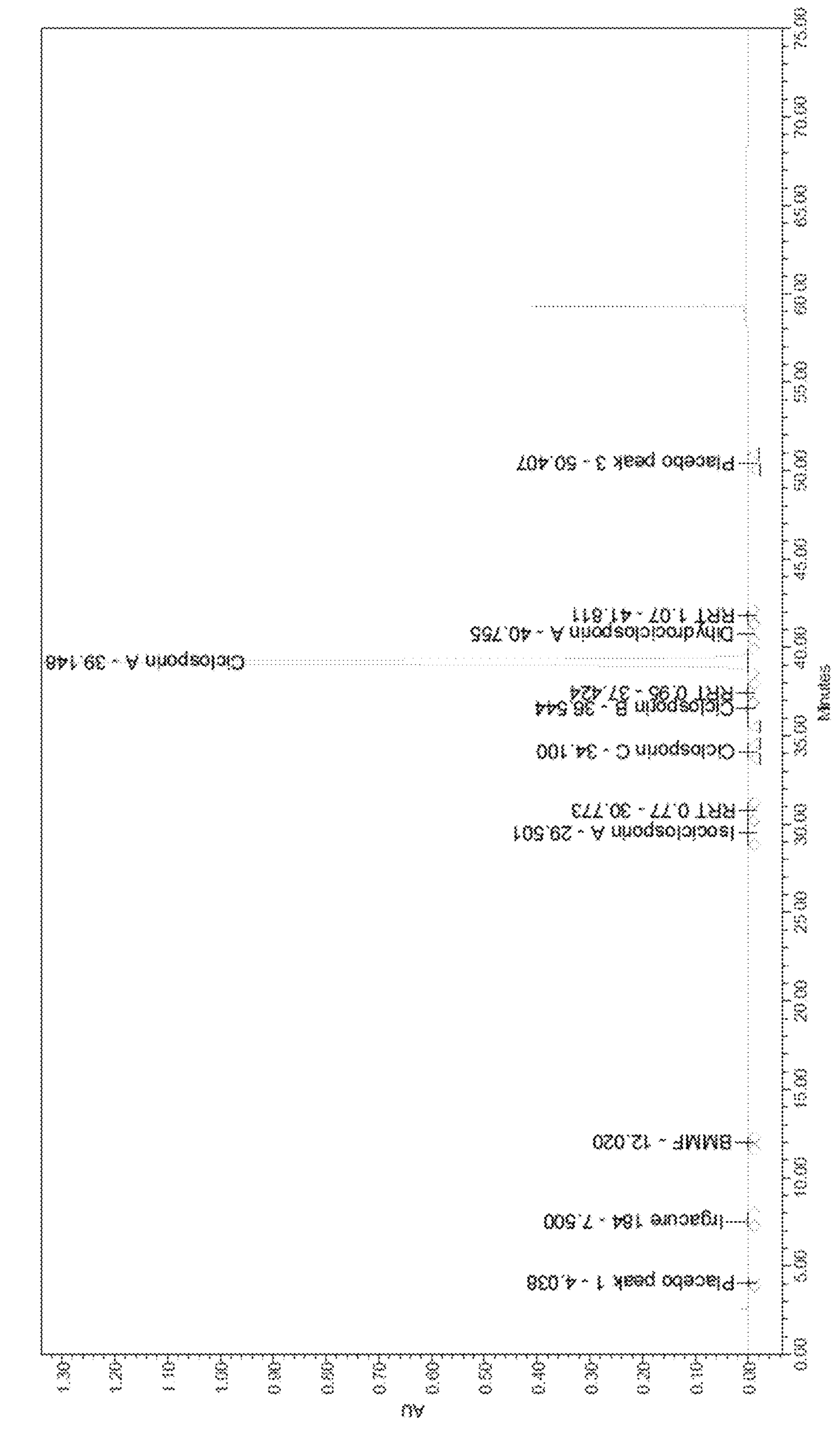
FIG. 4. HPLC chromatogram of Test Solution 1 of Example 4.

FIG. 4 shows a typical HPLC chromatogram of a sample solution (according to Test Solution 1 of Example 3) that is analyzed utilizing this analytical method.

Thus, the gradient is as follows:

| | min | | | | | |
|---|---|---|---|---|---|---|
| | 0 | 55 | 55.1 | 65 | 65.1 | 75 |
| mobile Phase A [%] | 65 | 40 | 10 | 10 | 65 | 65 |
| mobile Phase B [%] | 35 | 60 | 90 | 90 | 35 | 35 |

with:

mobile phase A: water, phosphoric acid 85% (100:0.08 VN)

mobile phase B: acetonitrile, phosphoric acid 85% (100:0.08 V/V).

In addition to the API-derived impurities quantified in Example 3, the method according to Example 4 further provides for the identification and/or quantification of certain leachable organic compounds derived from non-API related sources. These leachable compounds include 1-hydroxycyclohexyl phenyl ketone (a polymerization photoinitiator, sold as Irgacure® 184 by BASF), 9,9-bis(methoxymethyl)-9H-fluorene (a polymerization additive), and 3,3',3",5,5',5'-hexa-tert-butyl-alpha,alpha',alpha"-(mesitylene-2,4,6-triyl)-tri-p-cresol (a sterically hindered phenolic antioxidant used in polymers, and sold as Irganox® 1330 by BASF), Using this analytical method, the following typical retention times are found:

| | Retention Time (min) | Relative Retention Time |
|---|---|---|
| Cyclosporin A | 38.1 | 1.00 |
| Irgacure ® 184 | 7.0 | 0.13 |
| BMMF | 11.1 | 0.30 |
| Isocyclosporin A | 29.2 | 0.62 |
| Cyclosporin C | 33.1 | 0.87 |
| Cyclosporin B | 35.4 | 0.93 |
| Cyclosporin U | 37.0 | 0.98 |
| Cyclosporin H | 38.8 | 1.02 |
| Dihydrocyclosporin A | 39.6 | 1.05 |
| Cyclosporin D | 41.1 | 1.09 |
| Irganox ® 1330 | 58.7 | 1.58 |

The calculation of the relative retention time (RRT) is done according to USP<621>, Ph. Eur. 2.2.46.

In evaluating the purity of the API used in the Test Solution, any one or more of the above noted impurities/components may be evaluated. Preferably, the following: components are quantified: Cyclosporin A, Irgacure® 184 (1-hydroxycyclohexyl phenyl ketone), BMMF, isocyclosporin A, cyclosporin C, cyclosporin B, cyclosporin U, cyclosporin H, dihydrocyclosporin A, and cyclosporin D. Because the Irganox® 1330 peak (3,3',3",5,5',5'-hexa-tert-butyl-alpha,alpha',alpha"-(mesitylene-2,4,6-triyl)-tri-p-cresol) elutes during the column purge step according to the above method, this analyte is not quantified. However, with suitable modification of the column gradient and elution conditions, this analyte can be quantified as well.

We claim:

1. A method of determining the content of an active pharmaceutical ingredient (API) in a liquid pharmaceutical composition comprising the API dissolved in a liquid vehicle comprising semifluorinated alkane (SFA), wherein the API is cyclosporin A and wherein the SFA comprises 1-perfluorobutylpentane (F4H5), and wherein the method comprises a step of performing reverse-phase high-pressure liquid chromatography (RP-HPLC) and a step of removing a portion of the liquid vehicle of the composition before performing the RP-HPLC, and wherein the liquid vehicle further comprises ethanol, and wherein the composition is substantially free of water, and wherein the method further comprises the step of quantifying the content of the active pharmaceutical ingredient (API) comprised in the pharmaceutical composition.

2. The method according to claim 1, wherein the SFA comprises F4H5 (1-perfluorobutylpentane) and 2-perfluorobutylpentane.

3. The method according to claim 1, wherein the method comprises the step of removing all or substantially all of the liquid vehicle of the composition before performing the RP-HPLC.

4. The method according to claim 1, comprising the steps of:

(a) taking a representative sample of the pharmaceutical composition;

(b) removing a portion of the liquid vehicle from the pharmaceutical composition, to yield a residue;

(c) dissolving the residue in a suitable injection solvent to form the injection sample;

(d) causing the injection sample to be introduced onto a reverse-phase high-pressure liquid chromatography (HPLC) column comprising a stationary phase;

(e) causing a liquid mobile phase to run through the column in order to separate and elute the components of the pharmaceutical composition;

(f) detecting the components eluting off the column, using at least ultraviolet detection; and (g) determining the amount of the API in the pharmaceutical composition sample.

5. The method according to claim 4, wherein the quantification of the content of the active pharmaceutical ingredient (API) comprised in the pharmaceutical composition is based on integration of the peak area (area under the peak) of the peak corresponding to the active pharmaceutical ingredient (API) from the ultraviolet detection step (f).

6. The method according to claim 4, wherein the injection solvent of step (c) is a water-acetonitrile mixture.

7. The method according to claim 4, wherein the mobile phase of step (e) comprises an elution gradient of a water-acetonitrile mixture, followed by a column purge to return to initial conditions wherein the mobile phase further comprises about 0.05-0.10% v/v of an acid.

8. The method according to claim 7, wherein the mobile phase of step (e) comprises an elution gradient of a water-acetonitrile mixture running from 65% water/35% acetonitrile to 35% water/65% acetonitrile.

9. The method according to claim 4, wherein the stationary phase of step (d) of the column is a modified silica.

10. The method according to claim 9, wherein the modified silica is a high-purity porous silica having chemically bonded isopropyl and/or nitrile surface groups.

11. The method according to claim 4, wherein the detection of step (f) is performed using a 210 nm wavelength.

12. The method according to claim 4, wherein step (b) is performed by subjecting the sample to a stream of an inert gas to evaporate the SFA.

13. The method according to claim 1, wherein the removing of the liquid vehicle is performed by subjecting the sample to a stream of an inert gas to evaporate the SFA.

14. The method according to claim 1, wherein the pharmaceutical composition comprises up to about 1 wt. % ethanol.

15. The method according to claim 1, wherein the pharmaceutical composition comprises at least 90% by weight the SFA.

16. The method according to claim 1, wherein the pharmaceutical B composition comprises at least 97% by weight the SFA.

17. The method according to claim 1, wherein the pharmaceutical composition consists essentially of the cyclosporin A and the SFA, and ethanol.

18. The method according to claim 1, wherein the pharmaceutical composition consists of the cyclosporin A at a concentration of about 0.1% w/v dissolved in the F4H5 with up to about 1 wt. % ethanol.

19. The method according to claim 1, wherein the pharmaceutical composition consists of cyclosporin A at a concentration of about 0.10% w/v dissolved in not less than 97 wt. % F4H5, no more than 0.5 wt. % 2-perfluorobutylpentane and up to about 1 wt. % ethanol.

20. The method according to claim 1, wherein the pharmaceutical composition is formulated for and/or approved for use as a topical ophthalmic eye drop, for application to the surface of the cornea and/or the conjunctiva, for the treatment of keratoconjunctivitis sicca (dry eye disease), or the signs and symptoms of keratoconjunctivitis sicca (dry eye disease), or meibomian gland dysfunction (MGD), or any symptoms associated with the foregoing.

21. A method of manufacturing a liquid pharmaceutical composition comprising an active pharmaceutical ingredient (API) dissolved in a liquid vehicle comprising semifluorinated alkane (SFA), wherein the API is cyclosporin A and wherein the SFA comprises F4H5, and wherein the liquid vehicle further comprises ethanol, and wherein the composition is substantially free of water, wherein the method comprises carrying out the steps of:

(a) dissolving, suspending or dispersing the API in the SFA;

(b) adding ethanol and optionally any other pharmaceutically acceptable solvents or excipients;

(c) sterilizing and/or packaging the composition for distribution; and (d) analyzing a lot sample of the composition for the content of the API as recited in the method according to claim 1.

22. A method of determining the contents of a liquid pharmaceutical composition comprising an active pharmaceutical ingredient (API) dissolved in a liquid vehicle comprising semifluorinated alkane (SFA), wherein the method comprises a step of performing reverse-phase high-pressure liquid chromatography (RP-HPLC) and a step of removing a portion of the liquid vehicle of the composition before performing the RP-HPLC, and further comprising the steps of determining the content of API impurities derived from or related to the API, and leachable organic compounds in the pharmaceutical composition; wherein the API is cyclosporin A and wherein the SFA comprises F4H5, and wherein the liquid vehicle further comprises ethanol, and wherein the composition is substantially free of water.

23. A method of manufacturing a liquid pharmaceutical composition comprising an active pharmaceutical ingredient (API) dissolved in a liquid vehicle comprising semifluorinated alkane (SFA), wherein the API is cyclosporin A and wherein the SFA comprises F4H5, and wherein the liquid vehicle further comprises ethanol, and wherein the composition is substantially free of water, wherein the method comprises carrying out the steps of:

(a) dissolving, suspending or dispersing the API in the SFA;

(b) adding ethanol and optionally any other pharmaceutically acceptable solvents or excipients;

(c) sterilizing and/or packaging the composition for distribution; and (d) analyzing a lot sample of the composition for the content of the API as recited in the method according to claim 22.

24. The method according to claim 22, wherein the method comprises the steps of:

(a) taking a representative sample of the pharmaceutical composition;

(b) removing a portion of the liquid vehicle from the pharmaceutical composition, to yield a residue;

(c) dissolving the residue in a suitable injection solvent to form the injection sample;

(d) causing the injection sample to be introduced onto a reverse-phase high-pressure liquid chromatography (HPLC) column comprising a stationary phase;
(e) causing a liquid mobile phase to run through the column in order to separate and elute the components of the pharmaceutical composition;
(f) detecting the components eluting off the column, e.g., using at least ultraviolet detection; and
(g) identifying the components of and/or the purity of the pharmaceutical composition.

25. The method according to claim 22, wherein the method determines the content of components selected from cyclosporin A, impurities derived from or related to the cyclosporin A selected from the group consisting of isocyclosporin A, cyclosporin C, cyclosporin B, cyclosporin D, cyclosporin U, cyclosporin H, and dihydrocyclosporin A, or any and leachable organic compounds, and any combination thereof.

26. The method according to claim 25, wherein the leachable organic compounds are selected from the group consisting of 1-hydroxycyclohexyl phenyl ketone, 9,9-bis (methoxymethyl)-9H-fluorene (BMMF), and 3,3',3",5,5',5"-hexa-tert-butyl-alpha, alpha', alpha"-(mesitylene-2,4,6-triyl)-tri-p-cresol, and any combination thereof.

* * * * *